US007785851B2

(12) United States Patent
Goto et al.

(10) Patent No.: US 7,785,851 B2
(45) Date of Patent: *Aug. 31, 2010

(54) MUTANT PROTEIN HAVING DIAPHORASE ACTIVITY

(75) Inventors: Yoshio Goto, Kanagawa (JP); Taiki Sugiyama, Kanagawa (JP); Yuichi Tokita, Kanagawa (JP); Hideyuki Kumita, Kanagawa (JP); Jusuke Shimura, Tokyo (JP); Hideki Sakai, Kanagawa (JP); Takashi Tomita, Kanagawa (JP)

(73) Assignee: Sony Corporation, Tokyo (JP)

( * ) Notice: Subject to any disclaimer, the term of this patent is extended or adjusted under 35 U.S.C. 154(b) by 59 days.

This patent is subject to a terminal disclaimer.

(21) Appl. No.: 12/123,357

(22) Filed: May 19, 2008

(65) Prior Publication Data

US 2009/0155880 A1    Jun. 18, 2009

Related U.S. Application Data

(63) Continuation-in-part of application No. 12/121,501, filed on May 15, 2008, and a continuation-in-part of application No. 11/563,983, filed on Nov. 28, 2006, now abandoned.

(30) Foreign Application Priority Data

Nov. 29, 2005   (JP)   ............................. 2005-343605
Aug. 28, 2006   (JP)   ............................. 2006-231228

(51) Int. Cl.
   *C12N 9/02*   (2006.01)
   *C07H 21/04*  (2006.01)
(52) U.S. Cl. ...................................... 435/189; 536/23.2
(58) Field of Classification Search .................. None
   See application file for complete search history.

(56) References Cited

U.S. PATENT DOCUMENTS 6,146,862 A * 11/2000 Kawase et al. ............... 435/189
2009/0042232 A1 * 2/2009 Tokita et al. .................. 435/25

FOREIGN PATENT DOCUMENTS

JP   2004-071559   3/2004
JP   2004-298185   10/2007

OTHER PUBLICATIONS

Seffernick et al., Melamine deaminase and Atrazine chlorohydrolase: 98 percent identical but functionally different. J. Bacteriol.,2001, vol. 183 (8): 2405-2410.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Tokita et al., "Sony's biofuel cell," 213th ECS Meeting, Abstract #258, The Electrochemical Society, May 22, 2008.
Sugiyama et al., "Development of an Enzyme for the Biofuel Cell," Sony Corporation, 213th ECS Meeting, Abstract #204, The Electrochemical Society, May 19, 2008.
Tokita, Y. et al, "Sony's Biofuel Cell", ECS Transactions, 13 (21) pp. 89-97, May 23, 2008.

* cited by examiner

*Primary Examiner*—Ganapathirama Raghu
(74) *Attorney, Agent, or Firm*—K&L Gates LLP

(57) ABSTRACT

A mutant protein having diaphorase activity is provided. A mutant protein includes an amino acid sequence obtained by deletion, replacement, addition, or insertion of at least one amino acid residue of a native-form amino acid sequence of SEQ. ID. No. 1, wherein the mutant protein has diaphorase activity with an enzyme activity of 245 or more.

1 Claim, 13 Drawing Sheets

FIG. 4

| [ANQ] | DH"Amano"3 | G122D |
|---|---|---|
| $K_{M,ANQ}$ (mM) | 1.08 ± 0.22 | 0.356 ± 0.052 |
| $k_{cat}$ (s$^{-1}$) | 819 ± 75 | 838 ± 42 |
| $k_{cat}/K_{M,ANQ}$ (M$^{-1}$s$^{-1}$×10$^5$) | 7.57 ± 0.90 | 23.6 ± 2.5 |

| [NADH] | DH"Amano"3 | G122D |
|---|---|---|
| $K_{M,NADH}$ (mM) | 1.67 ± 0.23 | 2.20 ± 0.24 |
| $k_{cat}$ (s$^{-1}$) | 707 ± 24 | 707 ± 20 |
| $k_{cat}/K_{M,NADH}$ (M$^{-1}$s$^{-1}$×10$^5$) | 4.24 ± 0.49 | 3.22 ± 0.29 |

R147H, FRONT VIEW — FAD, Phe105, Asn104, Trp103

R147H, TOP VIEW — FAD, Phe105, Asn104, Trp103

G122D, FRONT VIEW — FAD, Phe105, Asn104, Trp103

G122D, TOP VIEW — FAD, Phe105, Asn104, Trp103

<WILD TYPE>

HYDROPHILIC

<R147H>

DISAPPEAR
HYDROPHILICITY

<G122D>

DISAPPEAR HYDROPHILICITY

<R147 (WILD TYPE)>
Tyt151  Aro147
His186
Vsi189
Ala188
Glu153  Glu158

<H147 (MUTANT)>
Gly149
Vsi189
His186
Glu153  His147

MUTANT PROTEIN HAVING DIAPHORASE ACTIVITY

CROSS REFERENCES TO RELATED APPLICATIONS

The present application is a continuation-in-part of application Ser. No. 12/121,501 filed on May 15, 2008 and is a continuation-in-part of application Ser. No. 11/563,983 filed on Nov. 28, 2006 now abandoned, which claims priority to Japanese Patent Application JP 2005-343605 filed in the Japanese Patent Office on Nov. 29, 2005, and Japanese Patent Application JP 2006-231228 filed in the Japanese Patent Office on Aug. 28, 2006, the entire contents of which are incorporated herein by reference.

BACKGROUND

The present application relates to a mutant protein having diaphorase activity. More specifically, the present application relates to a mutant protein having diaphorase activity and having predetermined levels or more of enzyme activity and heat resistance.

Enzymes are biocatalysts for allowing many reactions for the maintenance of life to smoothly proceed under mild conditions in vivo. Enzymes turn over in vivo, are produced in vivo according to need, and express their catalytic functions.

Techniques for making use of enzymes in vitro have already been used practically or studied to achieve practical use. For example, technology for using enzymes has been developed in various technical fields, such as the production of useful materials, the production of energy-related materials, measurement or analysis, environmental conservation, and medical care. In relatively recent years, technologies, such as an enzyme cell (for example, see Japanese Unexamined Patent Application Publication No. 2004-71559), which is a type of fuel cell, an enzyme electrode, and an enzyme sensor (sensor for measurement of a chemical substance using an enzymatic reaction), have been developed.

In general, enzymes are denatured by degrees of heat and pH. Hence, enzymes have low stability in vitro compared with other chemical catalysts such as metal catalysts. Accordingly, when enzymes are used in vitro, it is important to allow the enzymes to more stably work in response to environmental changes and to allow the activity of the enzymes to be maintained.

When an enzyme is used in vitro, a method for artificially modifying the nature and function of the enzyme and a method for producing the environment of the site in which the enzyme functions are employed. With respect to the former method, it is common that the base sequence of a gene encoding a protein is artificially modified, and the modified gene is expressed in an organism such as *Escherichia coli* to form an artificially mutated protein, and then the mutant protein having the target function and nature is separated by screening (for example, see Japanese Unexamined Patent Application Publication No. 2004-298185).

SUMMARY

In consideration of the wide availability of diaphorase in vitro, it is desirable to provide a mutant protein having predetermined levels of diaphorase activity and heat resistance.

According to an embodiment, there is provided a mutant protein including an amino acid sequence obtained by deletion, replacement, addition, or insertion of at least one amino acid residue of the native-form amino acid sequence of SEQ. ID. No. 1 (211 amino acid residues), wherein the mutant protein has diaphorase activity with an enzyme activity of 245 or more. Furthermore, there is provided a mutant protein having diaphorase activity in which enzyme activity is 245 or more, and residual activity is 27% or more and more preferably 41% or more after heating.

Furthermore, there is provided a mutant protein including an amino acid sequence obtained by deletion, replacement, addition, or insertion of at least one amino acid residue of a native-form amino acid sequence of SEQ. ID. No. 1, wherein the mutant protein has diaphorase activity with an enzyme activity of 170 or more and with residual activity of 41% or more after heating.

These mutant proteins are variants of proteins which have diaphorase activity and which are derived from, for example, thermophilic *Bacillus* bacteria, in particular, *Bacillus stearothermophilus*. More specifically, examples of the mutant proteins include mutant proteins having amino acid sequences of SEQ. ID. Nos. 2 to 56.

In the amino acid sequence of SEQ. ID. No. 2 (hereinafter, referred to as "K139N/A187E"), lysine at the 139th position from the N-terminus of the native-form amino acid sequence of SEQ. ID. No. 1 is replaced with asparagine, and alanine at the 187th position from the N-terminus is replaced with glutamic acid. In the amino acid sequence of SEQ. ID. No. 3 (hereinafter, referred to as "F105L"), phenylalanine at the 105th position from the N-terminus of the native-form amino acid sequence of SEQ. ID. No. 1 is replaced with leucine. In the amino acid sequence of SEQ. ID. No. 4 (hereinafter, referred to as "G122D"), glycine at the 122th position from the N-terminus of the native-form amino acid sequence of SEQ. ID. No. 1 is replaced with aspartic acid. In the amino acid sequence of SEQ. ID. No. 5 (hereinafter, referred to as "G131E"), glycine at the 131th position from the N-terminus of the native-form amino acid sequence of SEQ. ID. No. 1 is replaced with glutamic acid. In the amino acid sequence of SEQ. ID. No. 6 (hereinafter, referred to as "A146G"), alanine at the 146th position from the N-terminus of the native-form amino acid sequence of SEQ. ID. No. 1 is replaced with glycine. In the amino acid sequence of SEQ. ID. No. 7 (hereinafter, referred to as "R147H"), arginine at the 147th position from the N-terminus of the native-form amino acid sequence of SEQ. ID. No. 1 is replaced with histidine. In the amino acid sequence of SEQ. ID. No. 8 (hereinafter, referred to as "H34Q"), histidine at the 34th position from the N-terminus of the native-form amino acid sequence of SEQ. ID. No. 1 is replaced with glutamine. In the amino acid sequence of SEQ. ID. No. 9 (hereinafter, referred to as "F105H"), phenylalanine at the 105th position from the N-terminus of the native-form amino acid sequence of SEQ. ID. No. 1 is replaced with histidine. In the amino acid sequence of SEQ. ID. No. 10 (hereinafter, referred to as "A113E"), alanine at the 113th position from the N-terminus of the native-form amino acid sequence of SEQ. ID. No. 1 is replaced with glutamic acid.

In the amino acid sequence of SEQ. ID. No. 11 (hereinafter, referred to as "K123E"), lysine at the 123th position from the N-terminus of the native-form amino acid sequence of SEQ. ID. No. 1 is replaced with glutamic acid. In the amino acid sequence of SEQ. ID. No. 12 (hereinafter, referred to as "K139N"), lysine at the 139th position from the N-terminus of the native-form amino acid sequence of SEQ. ID. No. 1 is replaced with asparagine. In the amino acid sequence of SEQ. ID. No. 13 (hereinafter, referred to as "R147S"), arginine at the 147th position from the N-terminus of the native-form amino acid sequence of SEQ. ID. No. 1 is replaced with serine. In the amino acid sequence of SEQ. ID. No. 14 (hereinafter, referred to as "G149D"), lysine at the 149th position from the N-terminus of the native-form amino acid sequence of SEQ. ID. No. 1 is replaced with aspartic acid. In the amino acid sequence of SEQ. ID. No. 15 (hereinafter, referred to as "G154D"), glycine at the 154th position from the N-terminus of the native-form amino acid sequence of SEQ. ID. No. 1 is replaced with aspartic acid. In the amino acid sequence of SEQ. ID. No. 16 (hereinafter, referred to as "A156E"), alanine at the 156th position from the N-terminus of the native-form amino acid sequence of SEQ. ID. No. 1 is replaced with glutamic acid. In the amino acid sequence of SEQ. ID. No. 17 (hereinafter, referred to as "M159T"), methionine at the 159th position from the N-terminus of the native-form amino acid sequence of SEQ. ID. No. 1 is replaced with threonine. In the amino acid sequence of SEQ. ID. No. 18 (hereinafter, referred to as "A187E"), alanine at the 187th position from the N-terminus of the native-form amino acid sequence of SEQ. ID. No. 1 is replaced with glutamic acid. In the amino acid sequence of SEQ. ID. No. 19 (hereinafter, referred to as "A187T"), alanine at the 187th position from the N-terminus of the native-form amino acid sequence of SEQ. ID. No. 1 is replaced with threonine. In the amino acid sequence of SEQ. ID. No. 20 (hereinafter, referred to as "A187V"), alanine at the 187th position from the N-terminus of the native-form amino acid sequence of SEQ. ID. No. 1 is replaced with valine.

In the amino acid sequence of SEQ. ID. No. 21 (hereinafter, referred to as "R64H/A146T"), arginine at the 64th position from the N-terminus of the native-form amino acid sequence of SEQ. ID. No. 1 is replaced with histidine, and alanine at the 146th position is replaced with threonine. In the amino acid sequence of SEQ. ID. No. 22 (hereinafter, referred to as "E85D/R147H"), glutamic acid at the 85th position from the N-terminus of the native-form amino acid sequence of SEQ. ID. No. 1 is replaced with aspartic acid, and arginine at the 147th position is replaced with histidine. In the amino acid sequence of SEQ. ID. No. 23 (hereinafter, referred to as "F105L/A187E"), phenylalanine at the 105th position from the N-terminus of the native-form amino acid sequence of SEQ. ID. No. 1 is replaced with leucine, and alanine at the 187th position is replaced with glutamic acid. In the amino acid sequence of SEQ. ID. No. 24 (hereinafter, referred to as "A113E/K126N"), alanine at the 113th position from the N-terminus of the native-form amino acid sequence of SEQ. ID. No. 1 is replaced with glutamic acid, and lysine at the 126th position is replaced with asparagine. In the amino acid sequence of SEQ. ID. No. 25 (hereinafter, referred to as "Y151H/A187E"), tyrosine at the 151th position from the N-terminus of the native-form amino acid sequence of SEQ. ID. No. 1 is replaced with histidine, and alanine at the 187th position is replaced with glutamic acid. In the amino acid sequence of SEQ. ID. No. 26 (hereinafter, referred to as "G122D/A187E"), glycine at the 122th position from the N-terminus of the native-form amino acid sequence of SEQ. ID. No. 1 is replaced with aspartic acid, and alanine at the 187th position is replaced with glutamic acid. In the amino acid sequence of SEQ. ID. No. 27 (hereinafter, referred to as "G149D/A187E"), glycine at the 149th position from the N-terminus of the native-form amino acid sequence of SEQ. ID. No. 1 is replaced with aspartic acid, and alanine at the 187th position is replaced with glutamic acid. In the amino acid sequence of SEQ. ID. No. 28 (hereinafter, referred to as "G149S/A187E/L207W"), glycine at the 149th position from the N-terminus of the native-form amino acid sequence of SEQ. ID. No. 1 is replaced with serine, alanine at the 187th position is replaced with glutamic acid, and leucine at the 207th position is replaced with tryptophan. In the amino acid sequence of SEQ. ID. No. 29 (hereinafter, referred to as "F105L/A187E/L207W"), phenylalanine at the 105th position from the N-terminus of the native-form amino acid sequence of SEQ. ID. No. 1 is replaced with leucine, alanine at the 187th position is replaced with glutamic acid, and leucine at the 207th position is replaced with tryptophan. In the amino acid sequence of SEQ. ID. No. 30 (hereinafter, referred to as "G66R/F105L/A187E/K192R"), glycine at the 66th position from the N-terminus of the native-form amino acid sequence of SEQ. ID. No. 1 is replaced with arginine, phenylalanine at the 105th position is replaced with leucine, alanine at the 187th position is replaced with glutamic acid, and lysine at the 192th position is replaced with arginine.

In the amino acid sequence of SEQ. ID. No. 31 (hereinafter, referred to as "A146G/L207W"), alanine at the 146th position from the N-terminus of the native-form amino acid sequence of SEQ. ID. No. 1 is replaced with glycine, and leucine at the 207th position is replaced with tryptophan. In the amino acid sequence of SEQ. ID. No. 32 (hereinafter, referred to as "F105L/A187E/Q171P"), phenylalanine at the 105th position from the N-terminus of the native-form amino acid sequence of SEQ. ID. No. 1 is replaced with leucine, alanine at the 187th position is replaced with glutamic acid, and glutamine at the 171th position is replaced with proline. In the amino acid sequence of SEQ. ID. No. 33 (hereinafter, referred to as "A78E/F105L/A187E"), alanine at the 78th position from the N-terminus of the native-form amino acid sequence of SEQ. ID. No. 1 is replaced with glutamic acid, phenylalanine at the 105th position is replaced with leucine, and alanine at the 187th position is replaced with glutamic acid. In the amino acid sequence of SEQ. ID. No. 34 (hereinafter, referred to as "F105L/K149N/V168L/A187E"), phenylalanine at the 105th position from the N-terminus of the native-form amino acid sequence of SEQ. ID. No. 1 is replaced with leucine, lysine at the 149th position is replaced with asparagine, valine at the 168th position is replaced with leucine, and alanine at the 187th position is replaced with glutamic acid. In the amino acid sequence of SEQ. ID. No. 35 (hereinafter, referred to as "G154D/G180R"), glycine at the 154th position from the N-terminus of the native-form amino acid sequence of SEQ. ID. No. 1 is replaced with aspartic acid, and glycine at the 180th position is replaced with arginine. In the amino acid sequence of SEQ. ID. No. 36 (hereinafter, referred to as "F107I"), phenylalanine at the 107th position from the N-terminus of the native-form amino acid sequence of SEQ. ID. No. 1 is replaced with isoleucine. In the amino acid sequence of SEQ. ID. No. 37 (hereinafter, referred to as "G185R"), glycine at the 185th position from the N-terminus of the native-form amino acid sequence of SEQ. ID. No. 1 is replaced with arginine. In the amino acid sequence of SEQ. ID. No. 38 (hereinafter, referred to as "Y151H/G185R"), tyrosine at the 151th position from the N-terminus of the native-form amino acid sequence of SEQ. ID. No. 1 is replaced with histidine, and glycine at the 185th position is replaced with arginine. In the amino acid sequence of SEQ. ID. No. 39 (hereinafter, referred to as "Y151H/G185R"), glycine at the 122th position from the N-terminus of the native-form amino acid sequence of SEQ. ID. No. 1 is replaced with aspartic acid, and glycine at the 185th position is replaced with arginine. In the amino acid sequence of SEQ. ID. No. 40 (hereinafter, referred to as "G149D/G185R"), glycine at the 149th position from the N-terminus of the native-form amino acid sequence of SEQ. ID. No. 1 is replaced with aspartic acid, and glycine at the 185th position is replaced with arginine.

In the amino acid sequence of SEQ. ID. No. 41 (hereinafter, referred to as "G149D/G185R/A208V"), glycine at the 149th position from the N-terminus of the native-form amino acid sequence of SEQ. ID. No. 1 is replaced with aspartic acid, glycine at the 185th position is replaced with arginine, and alanine at the 208th position is replaced with valine. In the amino acid sequence of SEQ. ID. No. 42 (hereinafter, referred to as "F107I/G185R"), phenylalanine at the 107th position from the N-terminus of the native-form amino acid sequence of SEQ. ID. No. 1 is replaced with isoleucine, and glycine at the 185th position is replaced with arginine. In the amino acid sequence of SEQ. ID. No. 43 (hereinafter, referred to as "F107I/G185R/A208V"), phenylalanine at the 107th position from the N-terminus of the native-form amino acid sequence of SEQ. ID. No. 1 is replaced with isoleucine, glycine at the 185th position is replaced with arginine, and alanine at the 208th position is replaced with valine. In the amino acid sequence of SEQ. ID. No. 44 (hereinafter, referred to as "F107I/G185R/Q171P"), phenylalanine at the 107th position from the N-terminus of the native-form amino acid sequence of SEQ. ID. No. 1 is replaced with isoleucine, glycine at the 185th position is replaced with arginine, and glutamine at the 171th position is replaced with proline. In the amino acid sequence of SEQ. ID. No. 45 (hereinafter, referred to as "V80D/F107I/G185R"), valine at the 80th position from the N-terminus of the native-form amino acid sequence of SEQ. ID. No. 1 is replaced with aspartic acid, phenylalanine at the 107th position is replaced with isoleucine, and glycine at the 185th position is replaced with arginine. In the amino acid sequence of SEQ. ID. No. 46 (hereinafter, referred to as "F107I/K139N/V168L/G185R"), phenylalanine at the 107th position from the N-terminus of the native-form amino acid sequence of SEQ. ID. No. 1 is replaced with isoleucine, lysine at the 139th position is replaced with asparagine, valine at the 168th position is replaced with leucine, and glycine at the 185th position is replaced with arginine. In the amino acid sequence of SEQ. ID. No. 47 (hereinafter, referred to as "F150V"), phenylalanine at the 150th position from the N-terminus of the native-form amino acid sequence of SEQ. ID. No. 1 is replaced with valine. In the amino acid sequence of SEQ. ID. No. 48 (hereinafter, referred to as "A193E"), alanine at the 193th position from the N-terminus of the native-form amino acid sequence of SEQ. ID. No. 1 is replaced with glutamic acid. In the amino acid sequence of SEQ. ID. No. 49 (hereinafter, referred to as "F150V/A193E"), phenylalanine at the 150th position from the N-terminus of the native-form amino acid sequence of SEQ. ID. No. 1 is replaced with valine, and alanine at the 193th position is replaced with arginine. In the amino acid sequence of SEQ. ID. No. 50 (hereinafter, referred to as "Y151H/A193E"), tyrosine at the 151th position from the N-terminus of the native-form amino acid sequence of SEQ. ID. No. 1 is replaced with histidine, and alanine at the 193th position is replaced with glutamic acid.

In the amino acid sequence of SEQ. ID. No. 51 (hereinafter, referred to as "G122D/A193E"), glycine at the 122th position from the N-terminus of the native-form amino acid sequence of SEQ. ID. No. 1 is replaced with aspartic acid, and alanine at the 193th position is replaced with glutamic acid. In the amino acid sequence of SEQ. ID. No. 52 (hereinafter, referred to as "G149D/A193E/A208V"), glycine at the 149th position from the N-terminus of the native-form amino acid sequence of SEQ. ID. No. 1 is replaced with aspartic acid, alanine at the 193th position is replaced with glutamic acid, and alanine at the 208th position is replaced with valine. In the amino acid sequence of SEQ. ID. No. 53 (hereinafter, referred to as "F150V/A193E/A208V"), phenylalanine at the 150th position from the N-terminus of the native-form amino acid sequence of SEQ. ID. No. 1 is replaced with valine, alanine at the 193th position is replaced with glutamic acid, and alanine at the 208th position is replaced with valine. In the amino acid sequence of SEQ. ID. No. 54 (hereinafter, referred to as "F150V/A193E/Q171P"), phenylalanine at the 150th position from the N-terminus of the native-form amino acid sequence of SEQ. ID. No. 1 is replaced with valine, alanine at the 193th position is replaced with glutamic acid, and glutamine at the 171th position is replaced with proline. In the amino acid sequence of SEQ. ID. No. 55 (hereinafter, referred to as "V80D/F150V/A193E"), valine at the 80th position from the N-terminus of the native-form amino acid sequence of SEQ. ID. No. 1 is replaced with aspartic acid, phenylalanine at the 150th position is replaced with valine, and alanine at the 193th position is replaced with glutamic acid. In the amino acid sequence of SEQ. ID. No. 56 (hereinafter, referred to as "K139N/F150V/V168L/A193E"), lysine at the 139th position from the N-terminus of the native-form amino acid sequence of SEQ. ID. No. 1 is replaced with asparagine, phenylalanine at the 150th position is replaced with valine, valine at the 168th position is replaced with leucine, and alanine at the 193th position is replaced with glutamic acid.

The mutant proteins include a protein having an amino acid sequence obtained by deletion, replacement, addition, or insertion of at least one amino acid residue of any one of the amino acid sequences of SEQ. ID. Nos. 2 to 56 as well as the variant proteins having the amino acid sequences of SEQ. ID. Nos. 2 to 56.

Key technical terms related to the present invention will be described.

The term "diaphorase" means an enzyme having activity in which the enzyme catalyzes the oxidation of NADH or NADPH with dye, such as potassium ferricyanide, methylene blue, 2,6-dichloroindophenol, or a tetrazolium salt, i.e., the term "diaphorase" means an enzyme having diaphorase activity. The diaphorase is widely distributed in the range from microorganisms, such as bacteria and yeast, to mammals. The diaphorase plays an important part in an electron transport system in vivo. NADH or NADPH formed by dehydrogenation of a substrate caused by an NAD+- or NADP+-dependent dehydrogenase is oxidized by an electron acceptor in the presence of the diaphorase, resulting in a reduced form of the electron acceptor.

The term "mutant protein" means a protein expressed from a gene obtained by artificially modifying the base sequence in a DNA encoding an amino acid sequence constituting a protein.

The term "enzyme activity" generally means the catalytic rate of a reaction under a predetermined condition. In the present invention, the term "enzyme activity" means the catalytic rate of a reaction in which reduced nicotinamide dinucleotide (NADH) reduces 2-amino-1,4-naphthoquinone (ANQ) to yield oxidized nicotinamide dinucleotide (NAD+) and 2-amino-1,4-dihydroxynaphthalene. Specifically, the term "enzyme activity" is defined as the number of moles of a product resulting from a reaction catalyzed by one mole of an enzyme per unit time in a 0.1 M potassium phosphate buffer at 25° C. under an argon atmosphere or a nitrogen atmosphere in the presence of 0.3 mM ANQ and 40 mM NADH. Accordingly, the unit is sec$^{-1}$. Note that an enzyme activity of 245 or more corresponds to about 1.5 times or more that of a native protein having diaphorase activity and derived from *Bacillus stearothermophilus*.

The term "residual activity after heating" may also be referred to as "residual enzyme activity" or "retention of enzyme activity". The term "residual activity after heating" means a value representing a change in activity before and after an enzyme is subjected to predetermined heating. That is, enzyme activity is measured under the same condition before and after heating. The term "residual activity" means the percentage of activity after heating to activity before heating. In the present invention, the term "heating" means stationary treatment in a buffer solution at 80° C. for 10 minutes. The ratio of the enzyme activity after the heating to the enzyme activity before the heating is represented by percentage. Note that a residual activity of 41% or more corresponds to about 1.5 times or more that of a native protein having diaphorase activity and derived from *Bacillus stearothermophilus*.

A mutant protein according to an embodiment of the present invention has diaphorase activity and a predetermined level or more of enzyme activity and/or heat resistance.

Additional features and advantages are described herein, and will be apparent from, the following Detailed Description and the figures.

BRIEF DESCRIPTION OF THE FIGURES

FIG. 4 shows tables, as an alternative to drawings, summarizing factors that reflect ease of binding of substrates to active sites of wild-type diaphorase and G122D mutant diaphorase.

DETAILED DESCRIPTION

Figure 1:
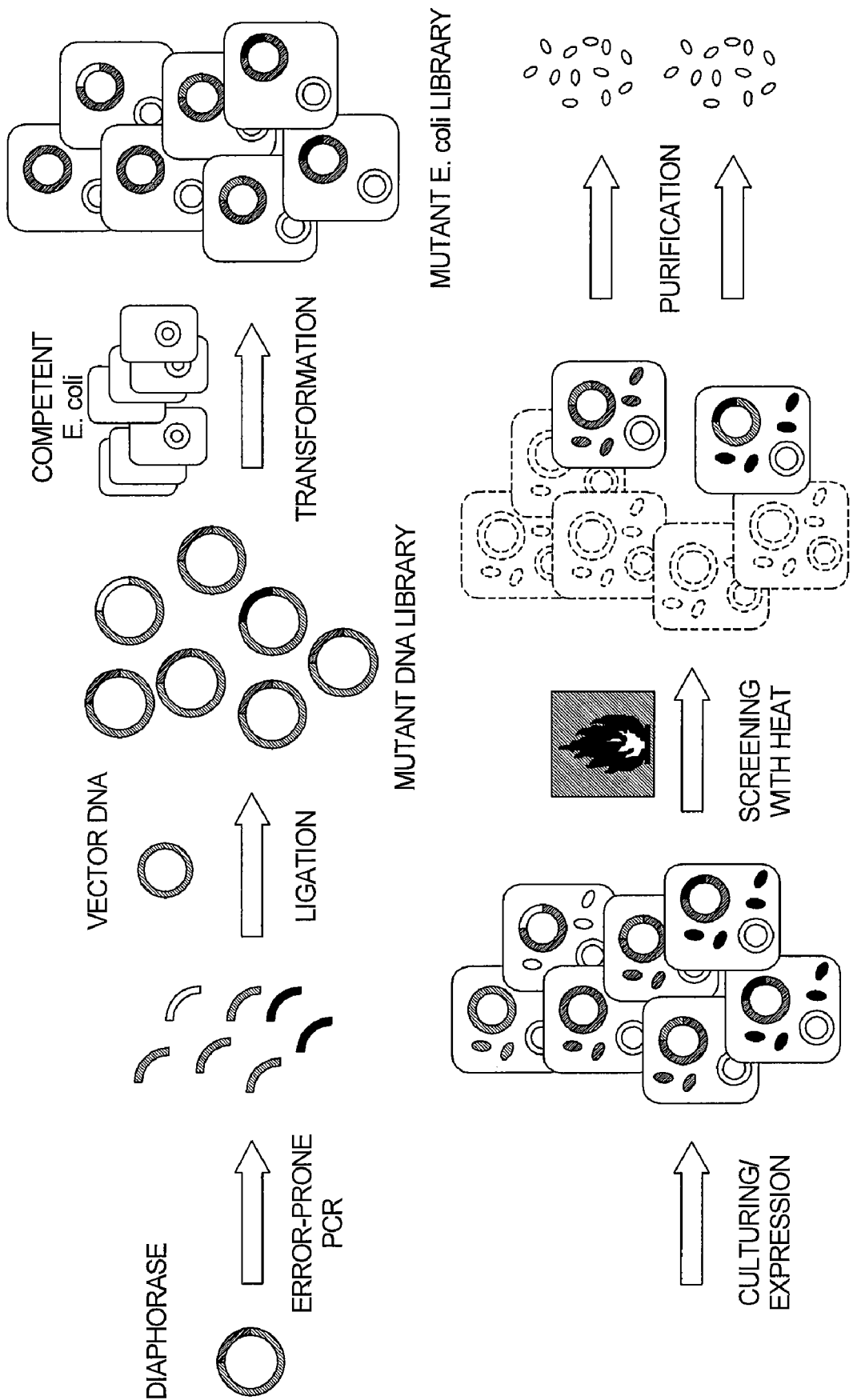
FIG. 1 is a diagrammatic illustration showing the flow of an experiment according to Example 2 (library preparation by random mutation and screening).

A description in further detail is provided below according to an embodiment.

Example 1

Cloning, Expression, and Purification of Diaphorase Derived From *Bacillus Stearothermophilus*

(1-1) Isolation and Purification of Genomic DNA from *Bacillus Stearothermophilus*

*Bacillus stearothermophilus* was purchased from Japan Collection of Microorganisms (JCM), Riken, (JCM No. 2501, NCBI accession number of a diaphorase gene: AF112858). A lyophilizate of *Bacillus stearothermophilus* was cultured on agar medium A overnight at 55° C.

The resulting colony was similarly cultured on fresh agar medium A to form a pure colony. The colony was partially picked up, cultured in liquid medium A overnight at 55° C., and centrifuged to collect the bacterium. Genomic DNA was isolated with a Wizard Genomic DNA Purification Kit (Promega Corporation) (Details on a process were given in an instruction manual included with a product). The composition of medium A was described in Table 1 (in 1 L, pH 7.0 to 7.2).

TABLE 1

| Meat Extract (Merck) | 10 g |
| Bacto Peptone (DIFCO) | 10 g |
| NaCl (Wako) | 5 g |
| Agar, guranulated (DIFCO) | 20 g (when an agar medium was made) |

(1-2) Cloning of Diaphorase Gene

A diaphorase gene was cloned by PCR from the genomic DNA obtained in item (1-1). Pfu DNA polymerase (Stratagene) was used as a DNA polymerase. A primer having sequences showing in Table 2 was used.

TABLE 2

| sense_DI | ggaattccat atgatgacaa acgtattgtac at | SEQ. ID. No. 57 |
| Antisense_DI | cgggatcctt aaaacgtgtg cgccaagt | SEQ. ID. No. 58 |

The resulting diaphorase gene, which was a PCR product, was purified with PCR Cleanup Kit (Qiagen) and verified by agarose gel electrophoresis. Furthermore, a base sequence was verified with a DNA sequencer.

(1-3) Introduction of Diaphorase Gene into Vector

Cloned fragments of the diaphorase gene were treated with BamH I and Nde I and purified with PCR Cleanup Kit (Qiagen). Vector pET12a (Novagen) was treated with BamH I and Nde I and purified similarly. These two types of fragments were ligated with T4 ligase. XL1-blue electrocompetent cells (Stratagene) were transformed with the resulting products and cultured in LB-amp medium to increase production.

The resulting plasmid was treated with Bss I. Insertion of the diaphorase gene was verified by agarose gel electrophoresis. The base sequence was measured and analyzed. The results showed a slight difference between the resulting base sequence and the base sequence stored in a database (NCBI). This was probably because the strain purchased from Japan Collection of Microorganisms (JCM), Riken, was slightly different from a strain described in the database, so that the base sequence of the cloned DI was inconsistent with the base sequence of the DI stored in the database. In the genotype (base sequence), there were inconsistencies at 11 points. Among these, in the phenotype (amino acid sequence), there were inconsistencies at two residues (see Table 3).

TABLE 3

| Amino acid residue No. | Resulting gene | Database |
|---|---|---|
| 28 | Glutamic acid | Aspartic acid |
| 61 | Aspartic acid | Glycine |

A gene was formed with Quick Change Site-Directed Mutagenesis Kit (Stratagene) so that the two amino acid residues were modified to be identical to those described in the database. This gene was named as "pET12a-BsDI".

(1-4) Transformation of E. Coli

The pET12a-BsDI was inserted and transformed into E. coli BL21 (DE3) (Novagen) by heat shock. After preculture in SOC for 1 hr at 37° C., the resulting transformant was developed on LB-amp agar medium. Part of the colonies was cultured in a liquid medium. The expression of diaphorase was verified by SDS-PAGE.

(1-5) Cryopreservation Sample of Transformant

First, 3 mL of a medium containing the transformant was centrifuged. E. coli pellets were suspended in 2XYT medium, and the resulting mixture was mixed and then stored at −80° C.

(1-6) Mass Culture and Purification of Protein

The frozen sample of BL21 (DE3)/pET12a-BsDI was developed on LB-amp agar medium. The resulting colony was picked up and precultured in 100 mL of LB-amp medium until OD600 reached about 1. The resulting preculture was developed in 18 L of LB-amp medium and cultured with shaking at 37° C. until OD600 was saturated about 2. The culture was centrifuged at 5 kG to harvest a bacterium (yield: 20 g, wet weight). The bacterial pellets were frozen at −80° C. and then melted. The bacterial pellets were treated by sonication at 0° C. in 200 mL of a solution containing 50 mM Tris-HCl (pH 7.8), 1 mM EDTA, 1 mM DTT, and 1 mM PMSF to cause bacteriolysis. The resulting lysate was centrifuged at 9.5 kG to recover a solution fraction.

Purification was performed by an ammonium sulfate precipitation method. Powdery ammonium sulfate was gradually added under stirring to form a 35% saturated solution. The solution was left standing overnight. Precipitates were removed by centrifugation at 9.5 kG. The solution was desalted with a dialysis membrane tube (final solution: 5 mM Tris-HCl, pH 7.8). Next, 50 mL of a sample concentrated by ultrafiltration was passed through an anion-exchange column (Sepharose Q FastFlow, Amersham Bioscience) to harvest a diaphorase-containing fraction. The resulting fraction was concentrated by ultrafiltration (the amount of the solution: 20 mL, Centriplus Centrifugal Filter Unit YM-30, Millipore). The resulting sample was passed through a gel filtration col- Example 2

Preparation of Mutant Library by Random Mutation of Diaphorase Derived from Bacillus Stearothermophilus and Screening of Thermostable Mutant FIG. 1 shows the flow of an experiment conducted in EXAMPLE 2. A gene library of a diaphorase mutant was constructed by error-prone PCR. The gene was introduced into vector DNA and expressed in E. coli. The resulting library was subjected to thermostability screening to extract a target thermostable diaphorase mutant.

(2-1) Error-Prone PCR with GeneMorph (Registered Trademark)

This is a method for randomly mutating cloned DNA fragments using misreading by a polymerase of a base sequence. A variety of methods have been reported. GeneMorph (registered trademark, Stratagene) was selected here among commercially available methods. The pET12a-BsDI integrated with the diaphorase gene of Bacillus stearothermophilus was used as a template DNA. A primer that was used for cloning this gene was also used.

Table 4 shows sequences of the primer. The primer has the sequence of Nde I at the 5' terminus of a coding strand and the sequence of BamH I at the 5' terminus of a complementary strand (underlined portion). Thus, error-prone PCR products can be inserted into a multicloning site of pET12a by treatment with these restriction enzymes (similar to the cloning of the native diaphorase).

TABLE 4

| sense_DI | ggaattccatatgatgacaaacgtattgtacat | SEQ. ID. No. 59 |
|---|---|---|
| Antisense_DI | cgggatccttaaaacgtgtgcgccaagt | SEQ. ID. No. 60 |

PCR was performed according to the manual of GeneMorph (registered trademark). Table 5 shows the composition of a reaction mixture. Table 6 shows a temperature profile.

TABLE 5

<Composition of reaction mixture>

| 41.5 µL | water |
|---|---|
| 5.0 µL | 10x Mutazyme reaction buffer |
| 1.0 µL | 40 mM dNTP mix (200 µM each final) |
| 0.5 µL | primer mix (250 ng/µL of each primer) |
| 1.0 µL | Mutazyme DNA polymerase (2.5 U/µL) |
| 1.0 µL | template (10 pg/µL-10 ng/µL) |
| 50.0 µL | in total |

TABLE 6

<Temperature profile>

| Segment | Number of cycle | Temperature | duration |
|---|---|---|---|
| 1 | 1 | 96° C. | 30 sec |
| 2 | 30 | 96° C. | 30 sec |
|   |   | 53° C.*[1] | 30 sec |
|   |   | 72° C. | 1 min*[2] |
| 3 | 1 | 72° C. | 10 min |

*[1]Primer Tm −5° C.
*[2]1 min for ≦1 kb target (2-2) Introduction of Diaphorase Gene into Vector The total amount of the error-prone PCR products other than the amount of the products used for agarose gel electrophoresis was used for the treatment with the restriction enzymes, Nde I and BamH I. After the reaction was performed at 37° C. for 2 hours, the resulting reaction product was purified with Qiaquick PCR purification Kit (Qiagen). The vector pET12a was treated with the restriction enzymes, Nde I and BamH I, in the same way as the PCR products (at 37° C. for 2 hours).

The reaction products resulting from the treatment with the restriction enzymes were separated by low-melting-point agarose gel electrophoresis. The target open-circular vector DNA was purified with Qiaquick Gel Extraction Kit (Qiagen). The products purified by treatment of the vector with the restriction enzymes were treated with an alkaline phosphatase to dephosphorylate the 5' terminus. The reaction products were purified with Qiaquick PCR purification Kit (Qiagen). The resulting error-prone PCR products, i.e., diaphorase mutant gene library, were ligated into the vector that was treated with the restriction enzymes and dephosphorylated. A ligation reaction was performed with Ligation Kit Mighty Mix (Takara Bio Inc). The reaction product was purified by ethanol precipitation.

(2-3) Preparation of Competent Cell and Transformation

Electrocompetent cells (competency: about $10^8$/ng) of in-house prepared BL21 (DE3) were used as competent cells. Next, 40 μL of the competent cell frozen sample was melted on ice, and 0.5 μL of the DNA sample having a concentration of about 1 ng/μL was mixed thereto. The total mixture was charged into an electroporation cuvette with a gap of 0.1 cm. Transformation was performed by applying 1,800 kV. Then, 960 μL of an SOC medium was added thereto. The resulting mixture was precultured by shaking for 1 hour at 37° C. The resulting culture was inoculated on 5 to 50 μL of LB-amp agar medium and incubated at 37° C. overnight.

(2-4) Screening Method

Each colony on the agar medium obtained in item (2-3) was inoculated using a toothpick into LB-amp liquid medium (150 μL) on 96-well plate. Two wells were occupied by a strain of E. coli that produces a wild type. The top of the well plate was sealed with a gas-permeable adhesive sheet (ABgene) and covered with an accompanying lid. The cultures were cultured with shaking at 37° C. overnight (about 14 hours). Next, 25 μL each of the resulting cultures was placed into 25 μL of a 0.2 N NaOH aqueous solution that has been aliquoted in another well plate. After the mixture was well mixed by pipetting, the plate was covered with a lid and incubated at 37° C. for 15 minutes with an incubator to cause bacteriolysis.

Next, 100 μL of 0.1 M K-pi (pH 6.8) was added thereto at room temperature to neutralize the mixture. One of the two wild-type samples was separated, charged into a microtube, and stored at room temperature, the sample being used as an unheated control sample. The plate was sealed with a commercially available OPP tape, heated at 80° C. for 75 minutes with an incubator, and left standing to cool to room temperature. The separated wild-type sample was returned to the plate. Then, 10 μL of a 20 mM anthraquinone sulfonic acid (AQS) in a 20% DMSO solution and 50 μL of a 80 mM NADH aqueous solution prepared just before using it were added to each sample. The plate was sealed with the OPP tape and stirred for 5 seconds with a vortex mixer. Revelation was recorded with a camera. Samples having strong coloration due to reduction of AQS compared with the coloring of the wild-type sample were selected as candidates for thermostable mutants.

(2-5) Preservation of Sample

In the samples selected from the screening, part of each culture remaining in the 96-well plate was inoculated into 4.5 mL of LB medium and cultured overnight. The plasmid was purified and stored in a freezer. Furthermore, each culture was separately inoculated into 4 mL of LB medium and cultured until O.D. 600 reached about 0.4 and centrifuged to collect a bacterium. The resulting bacterium was suspended in 2 mL of 2xYT medium, frozen with liquid nitrogen, and preserved at −80° C.

(2-6) Abundant Expression and Purification of Diaphorase Mutant

Abundant expression and purification of a diaphorase mutant were performed by a method described above. In the abundant expression, E. coli was cultured in 1 L of LB-amp medium. The volume and the like in the following purification steps were adjusted according to a culture scale.

(2-7) Activity Evaluation Test

Activity evaluation of a diaphorase mutant was performed under the conditions described below. A reaction solution contained 100 mM K-pi (pH 8.0), [ANQ]=0.3 mM, [NADH]=40 mM, and [diaphorase]=48 nM. Deoxygenation was sufficiently performed by argon bubbling before measurement. The reaction was performed under argon atmosphere. The addition of diaphorase initiated the reaction. The extent of reaction was monitored by means of a reduction in the absorbance of ANQ at 520 nm (molar absorption coefficient: 680 $M^{-1}$ $cm^{-1}$) to calculate the reaction rate.

(2-8) Heat Resistance Test

A purified diaphorase mutant sample solution in 50 mM Tris-HCl (pH 7.8) and a 300 mM NaCl solution was concentrated by ultrafiltration, and the buffer was replaced to prepare a 0.1 M K-pi (pH 8.0) solution. This solution was appropriately diluted in such a manner that the absorbance of diaphorase at 460 nm was 0.1 (the solution with an enzyme concentration of 8.3 μM). This solution was incubated at 80° C. for 10 minutes with an aluminum block heater or the like and immediately cooled on ice. Activity was measured after sufficiently cooled. A control experiment was made with a sample that was not incubated.

(2-9) Result

Figure 2:
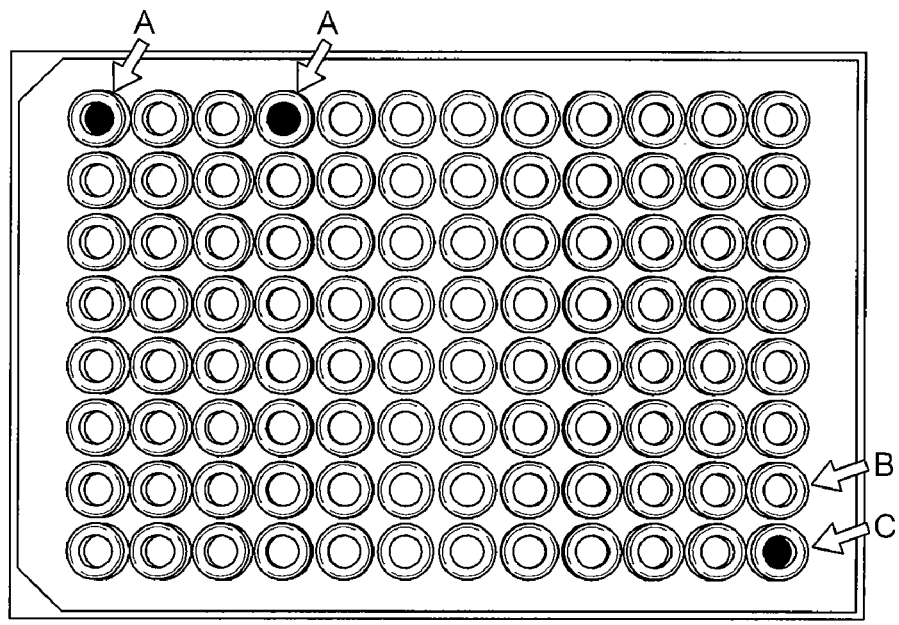
FIG. 2 is part of an illustration of a well plate when a total of about 8,000 colonies are screened.

A total of about 8,000 colonies were screened according to the above-described method. FIG. 2 is part of an illustration of a well plate used in this Example. FIG. 2 shows an example of the detection of diaphorase maintaining activity during screening. Arrows A and A indicate samples of candidates of thermostable mutants detected in this plate. Arrow B indicates a wild-type sample as a control. Arrow C indicates a wild-type sample that is not subjected to heat treatment.

In consideration of possible errors, such as the variation between plates and difference in level of expression between strains, selected samples were screened again. That is, cryopreserved E. coli samples were streak-cultured on LB agar medium. The resulting colonies were inoculated on a 96-well plate and heated similarly. However, in order to minimize the error, 8 colonies per sample were screened.

Figure 3:
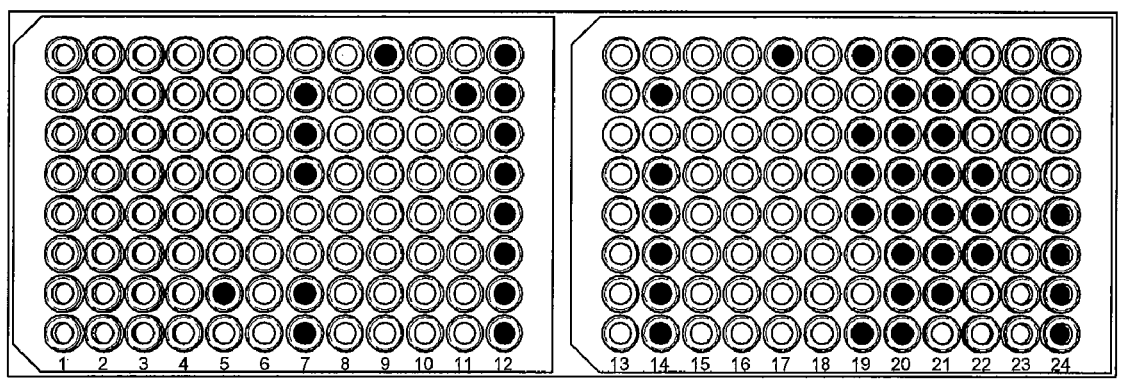
FIG. 3 is part of an illustration of a well plate resulting from a double check experiment.

FIG. 3 is part of an illustration of a well plate resulting from a double check experiment. In FIG. 3, the same mutant sample was disposed along a column. As a control, the wild-type sample after heat treatment was disposed at column 11 and 4 wells located at the upper side of column 24, and the wild-type sample not subjected to heat treatment was disposed at column 12 and 4 wells located at the lower side of column 24. In this example of the illustration shown in FIG. 3, samples disposed columns 7, 14, 17, 19, 20, and 21 were positive. The samples were selected as candidates for thermostable mutants.

Tables 7 to 12 show results of the heat resistance test of the candidates for the thermostable diaphorase mutants.

TABLE 7

| SEQ. ID. No. | Type of mutant | Activity ($S^{-1}$) | Residual activity (%) |
|---|---|---|---|
| 1 | WT (wild type, control) | 168 | 23 |
| 2 | K139N/A187E | 367 | 53 |
| 3 | F105L | 246 | 48 |
| 4 | G122D | 362 | 28 |
| 5 | G131E | 250 | 28 |
| 6 | A146G | 263 | 9 |
| 7 | R147H | 315 | 4 |
| 8 | H34Q | 228 | 8 |
| 9 | F105H | 283 | 33 |
| 10 | A113E | 143 | 46 |

TABLE 8

| SEQ. ID. No. | Type of mutant | Activity ($S^{-1}$) | Residual activity (%) |
|---|---|---|---|
| 11 | K123E | 155 | 34 |
| 12 | K139N | 263 | 25 |
| 13 | R147S | 226 | 17 |
| 14 | G149D | 168 | 22 |
| 15 | G154D | 247 | 24 |
| 16 | A156E | 318 | 27 |
| 17 | M159T | 196 | 28 |
| 18 | A187E | 407 | 52 |
| 19 | A187T | 328 | 17 |
| 20 | A187V | 214 | 33 |

TABLE 9

| SEQ. ID. No. | Type of mutant | Activity ($S^{-1}$) | Residual activity (%) |
|---|---|---|---|
| 21 | R64H/A146T | 169 | 20 |
| 22 | E85D/R147H | 321 | 37 |
| 23 | F105L/A187E | 241 | 46 |
| 24 | A113E/K126N | 211 | 31 |
| 25 | Y151H/A187E | 284 | 20 |
| 26 | G122D/A187E | 356 | 61 |
| 27 | G149D/A187E | 215 | 53 |
| 28 | G149S/A187E/L207W | 212 | 38 |
| 29 | F105L/A187E/L207W | 524 | 15 |
| 30 | G66R/F105L/A187E/K192R | 428 | 24 |

TABLE 10

| SEQ. ID. No. | Type of mutant | Activity ($S^{-1}$) | Residual activity (%) |
|---|---|---|---|
| 31 | A146G/L207W | 213 | 15 |
| 32 | F105L/A187E/Q171P | 283 | 68 |
| 33 | A78E/F105L/A187E | 284 | 68 |
| 34 | F105L/K149N/V168L/A187E | 270 | 55 |
| 35 | G154D/G180R | 297 | 33 |
| 36 | F107I | 283 | 53 |
| 37 | G185R | 446 | 58 |
| 38 | Y151H/G185R | 315 | 15 |
| 39 | G122D/G185R | 387 | 63 |
| 40 | G149D/G185R | 264 | 54 |

TABLE 11

| SEQ. ID. No. | Type of mutant | Activity ($S^{-1}$) | Residual activity (%) |
|---|---|---|---|
| 41 | G149D/G185R/A208V | 223 | 26 |
| 42 | F107I/G185R | 305 | 48 |
| 43 | F107I/G185R/A208V | 545 | 73 |
| 44 | F107I/G185R/Q171P | 410 | 21 |
| 45 | V80D/F107I/G185R | 437 | 72 |
| 46 | F107I/K139N/V168L/G185R | 283 | 47 |
| 47 | F150V | 380 | 58 |
| 48 | A193E | 497 | 63 |
| 49 | F150V/A193E | 412 | 51 |
| 50 | Y151H/A193E | 358 | 18 |

TABLE 12

| SEQ. ID. No. | Type of mutant | Activity ($S^{-1}$) | Residual activity (%) |
|---|---|---|---|
| 51 | G122D/A193E | 418 | 68 |
| 52 | G149D/A193E/A208V | 275 | 30 |
| 53 | F150V/A193E/A208V | 572 | 78 |
| 54 | F150V/A193E/Q171P | 458 | 43 |
| 55 | V80D/F150V/A193E | 512 | 82 |
| 56 | K139N/F150V/V168L/A193E | 294 | 37 |

For example, in mutant proteins having the amino acid sequence of SEQ. ID. Nos. 2 to 7, 9, 12, 15, 16, 18, 19, 22, 25, 26, 29, 30, 32 to 40, and 42 to 56, enzyme activity (reaction rate) was significantly improved compared with the wild type (WT). Furthermore, for example, in mutant proteins having the amino acid sequence of SEQ. ID. Nos. 2, 3, 18, 23, 26, 27, 32 to 34, 36, 37, 39, 40, 42, 43, 45 to 49, 51, and 53 to 55, residual activity after heat treatment was particularly satisfactory compared with the wild type (WT).

Furthermore, in this experimental system, a target diaphorase mutant having improved thermostability was successfully prepared. Accordingly, the method for constructing a mutant library by random mutation using error-prone PCR and the method of screening by heat treatment were practically useful.

Example 3

Detailed Study of Thermostable Diaphorase Mutant

Among the mutants obtained by the above-described study, with respect to G122D in which enzyme activity was improved compared with the wild type, a study based on enzyme kinetics was conducted.

The enzymatic reaction rate was plotted against the concentration of ANQ in the presence of NADH 40 mM. Furthermore, the enzymatic reaction rate was plotted against the concentration of NADH in the presence of 2.2 mM ANQ. The results were well consistent with the Michaelis-Menten equation. Then, kcat, KM (NADH), and KM (ANQ) were determined on the basis of the equation.

Kcat, KM (NADH), and KM (ANQ) of wild-type (native) diaphorase (DI (DH "Amano" 3)) are shown for comparison. Diaphorase shows a ping-pong reaction mechanism. The term "kcat" means a turnover number per unit time in a catalytic reaction. The terms "KM (NADH)" and "KM (ANQ)" refer to Michaelis constants for substrates and are factors that reflect ease of binding of substrates to active sites of the enzymes. FIG. 4, as an alternative to tables, summarizes the results.

The results demonstrates that the mediator ANQ binding site of the mutant has a property of ease of bonding compared with the wild type (native) (see ANQ association table in FIG. 4). On the other hand, with respect to the NADH binding site, factors were not different from those of the wild type (native) or may be reduced (see NADH association table in FIG. 4). Thus, it can be predicted that the higher catalytic ability of the mutant (mutant protein) is attributed to the acquisition of affinity for the ANQ substrate.

This means that the mutant does not exhibit higher catalytic activity at higher concentrations but exhibits an advantage at low concentrations. For example, this may lead to an advantage that the concentration of the mediator ANQ in an enzyme battery can be suppressed.

Example 4

Study by Molecular Dynamics Simulation

In this Example, the conformation of each mutant protein R147H and G122D was estimated by molecular dynamics simulation. The conformation of the wild-type protein was compared with that of the mutant protein. The relationship among the conformation of the mutant diaphorase, enzyme activity thereof, and thermostability was studied.

General information on the computation and computational model of the molecular dynamics simulation is described below.

In this simulation, commercially available protein modeling software, "Discovery Studio Modeling" (hereinafter, referred to as "DS Modeling") was used. In the simulation, "DS Modeling 1.1" was used for initial modeling of the conformation of a protein, and "DS Modeling 1.5" was used for calculation and analysis using a force field.

With respect to the wild-type diaphorase, similarity search was performed by position specific iterative BLAST (PST-BLAST) to make a search for a protein having high similarity. Then, a protein having the highest score in the search was used as a template, and the initial modeling of the wild-type diaphorase and mutant diaphorase was performed by 3-D Alignment. Initial modeling of a coenzyme (FAD) was also performed.

With respect to the initial modeling, the chemistry at harvard macromolecular mechanics (CHARMm) force field was assigned to each atom, and the structure was optimized by molecular mechanics calculation. The structure was optimized by 1,000 steps of calculation using the steepest-descent method and then 5,000 steps of calculation using the adapted basis Newton-Raphson method.

In order to consider thermodynamic conditions, the set condition was changed from 50 K to 300 K through 2,000 steps (1 step was 1 femtosecond). Then, the structure at 300 K was calculated.

The number of particles n, a volume V, and a temperature T were set at a constant (NVT ensemble). Equilibration calculation at 300 K was performed for 1 nanosecond (1 step is 1 femtosecond).

Molecular dynamics (MD) calculation was performed for 1 nanosecond (1 step was 1 femtosecond). The motion of each atom was tracked to perform energetic analysis.

Thereby, the conformation of each of the wild-type diaphorase and the mutant diaphorase was simulated through the above-described steps. FIGS. 5 to 11 show the results.

Figure 5:
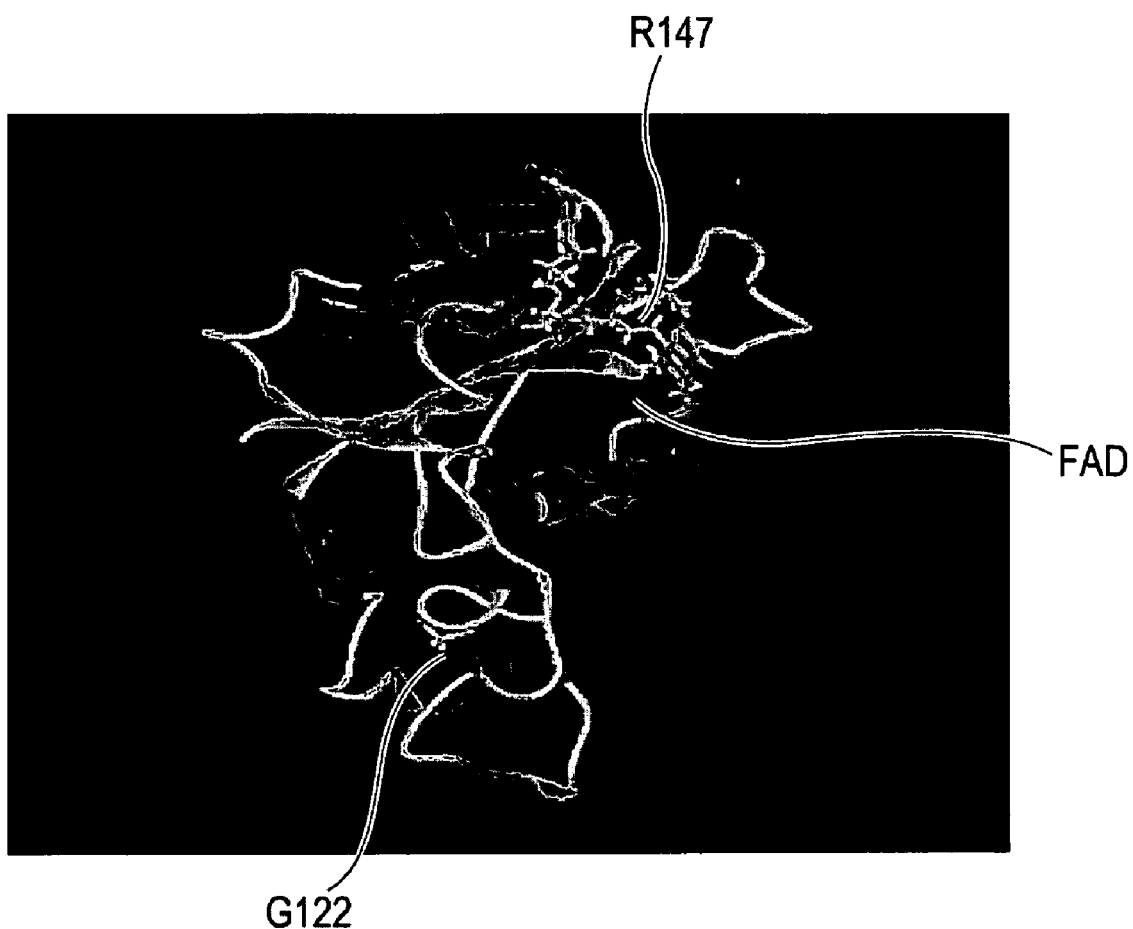
FIG. 5 shows a conformation observed by simulation of wild-type diaphorase.

FIG. 5 shows a conformation observed by simulation of wild-type diaphorase. This conformation is a final structure after MD calculation. In FIG. 5, "FAD" indicates the site of FAD (coenzyme). "R147" and "G122" each indicate the site of an amino acid residue replaced in the mutant protein.

As shown in FIG. 5, "R147" is located in the vicinity of FAD, i.e., "R147" is located in the vicinity of an active site for an enzymatic reaction. "G122" is located at a position remote from the active site for the enzymatic reaction. However, "G122" is present at a position at which three α-helices gather and is present at an important position in the conformation of the protein.

FIGS. 6A to 7B are each a photograph, as an alternative to a drawing, showing the results of structure analysis in the vicinity of the active site of the enzymatic reaction.

Figure 6A:
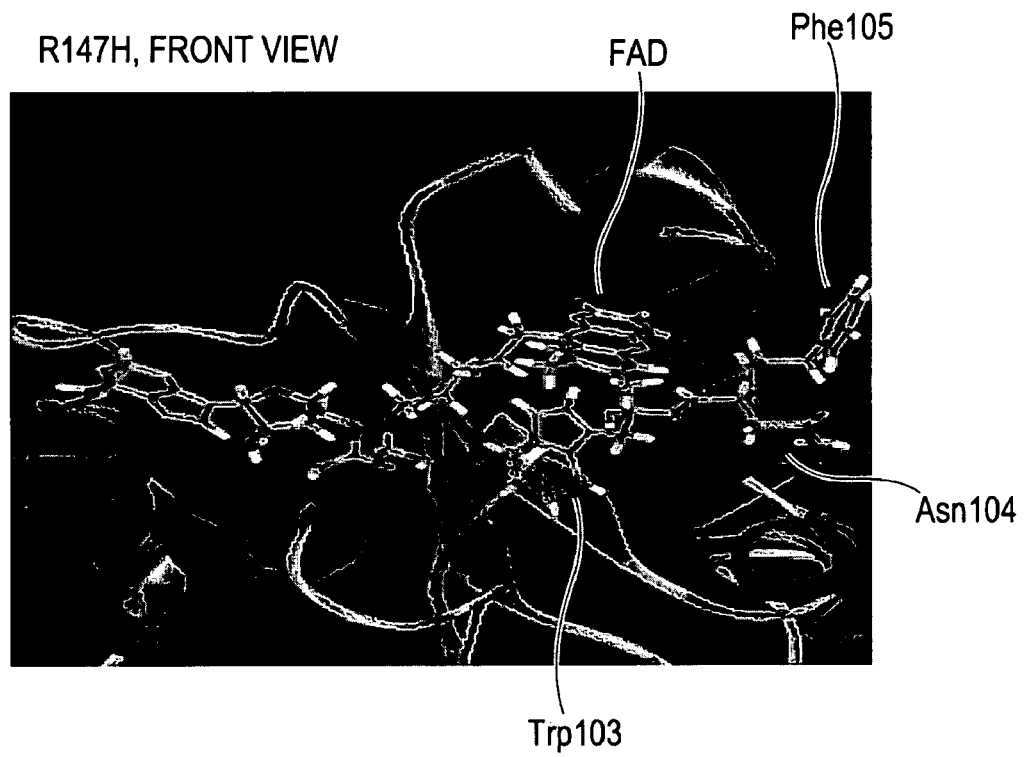
FIG. 6A is a front structural view illustrating the vicinity of FAD in the conformation obtained by simulation of R147H mutant diaphorase.
Figure 6B:
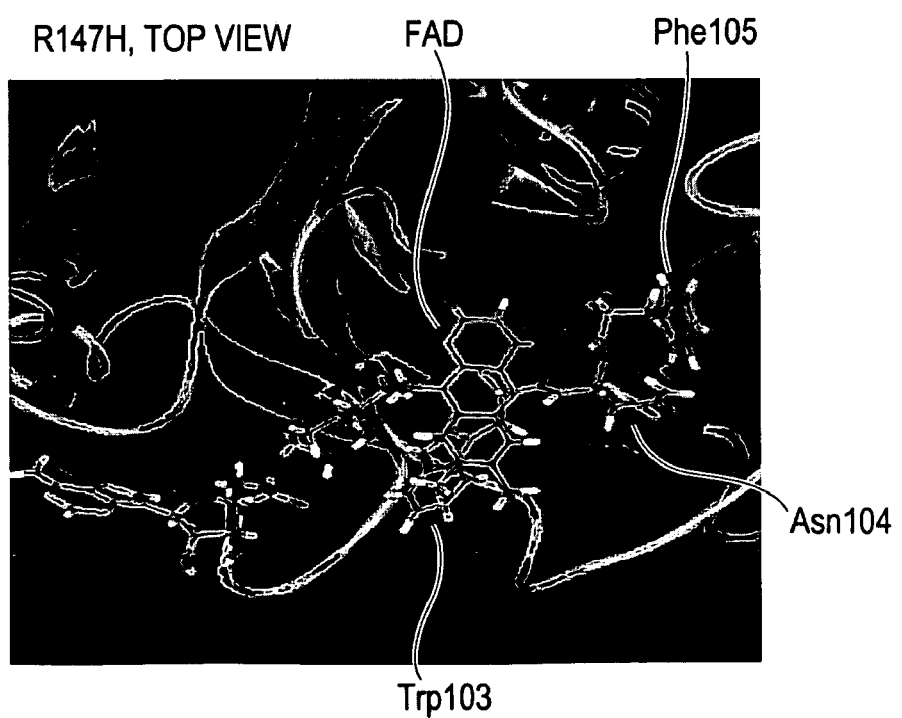
FIG. 6B is a top structural view illustrating the vicinity of FAD in the conformation obtained by simulation of R147H mutant diaphorase.
Figure 7A:
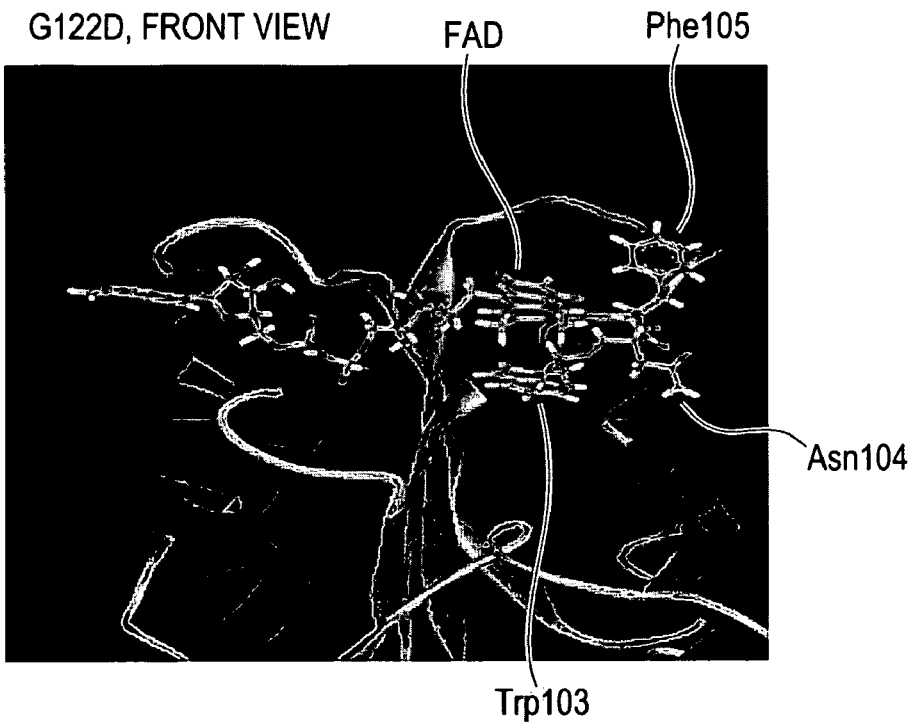
FIG. 7A is a front structural view illustrating the vicinity of FAD in the conformation obtained by simulation of G122D mutant diaphorase.
Figure 7B:
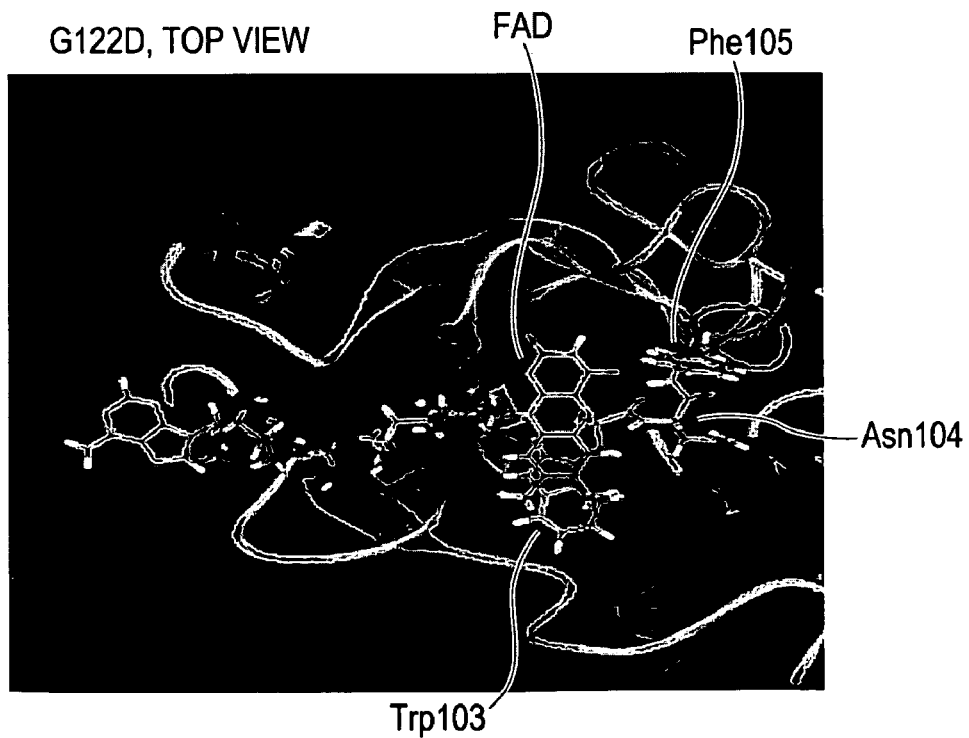
FIG. 7B is a top structural view illustrating the vicinity of FAD in the conformation obtained by simulation of G122D mutant diaphorase.

FIGS. 6A and 6B each show the vicinity of FAD in the conformation of R147H mutant diaphorase obtained by simulation. FIGS. 7A and 7B each show the vicinity of FAD in the conformation of G122D mutant diaphorase. FIGS. 6A and 7A are each a front structural view. FIGS. 6B and 7B are each a top structural view.

In the above-described enzyme activity analysis, the simulated mutant protein had high enzyme activity (reaction rate) compared with the wild-type diaphorase. On the other hand, as shown in FIGS. 6A to 7B, mutant diaphorase is different in the position of Trp103 from wild-type diaphorase (see FIG. 5).

That is, Trp103 in the wild type is remote from flavin in FAD, whereas Trp103 in the mutant is located below flavin. As a result, Asn104 in the wild type is located above the plane of flavin and is thus close to the active center (N atom disposed at the middle) of flavin, whereas Asn104 in the mutant is located below the plane of flavin and is thus remote from the active center of flavin.

The results suggest that in the conformation of diaphorase, mutation such that the amino acid residue (Asn104) located at the 104th position of the amino acid sequence is remote from the active center of flavin of coenzyme FAD improves the enzyme activity of diaphorase. That is, the results suggest that in the conformation of diaphorase, the enzyme activity of the mutant protein having a modified structure in which the amino acid residue located at the 104th position of the amino acid sequence is remote from the active center of flavin of coenzyme in the conformation is higher than that of the wild-type diaphorase.

Figure 8:
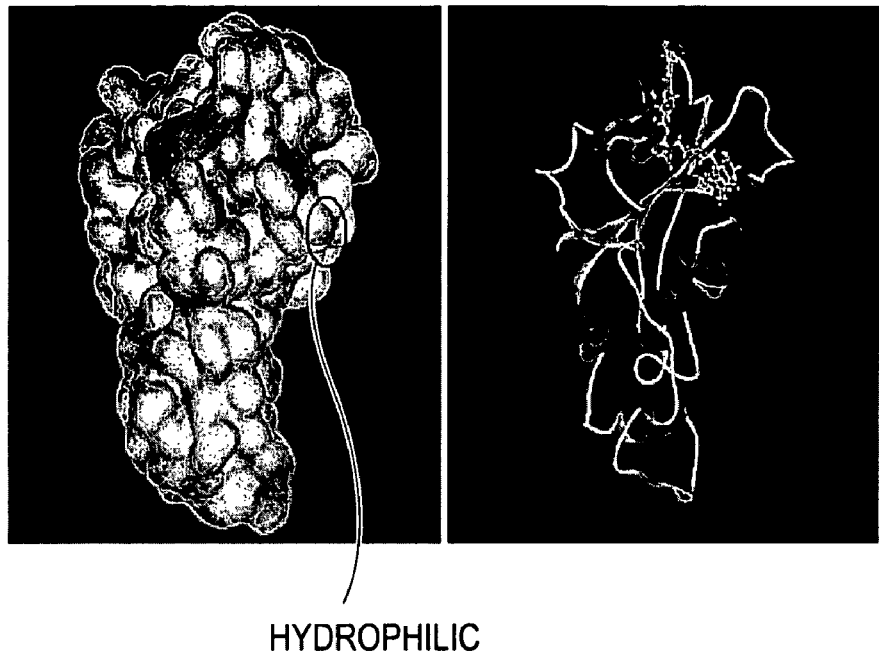
FIG. 8 shows the electrostatic potential surface and the conformation obtained by simulation of wild-type diaphorase.
Figure 9:
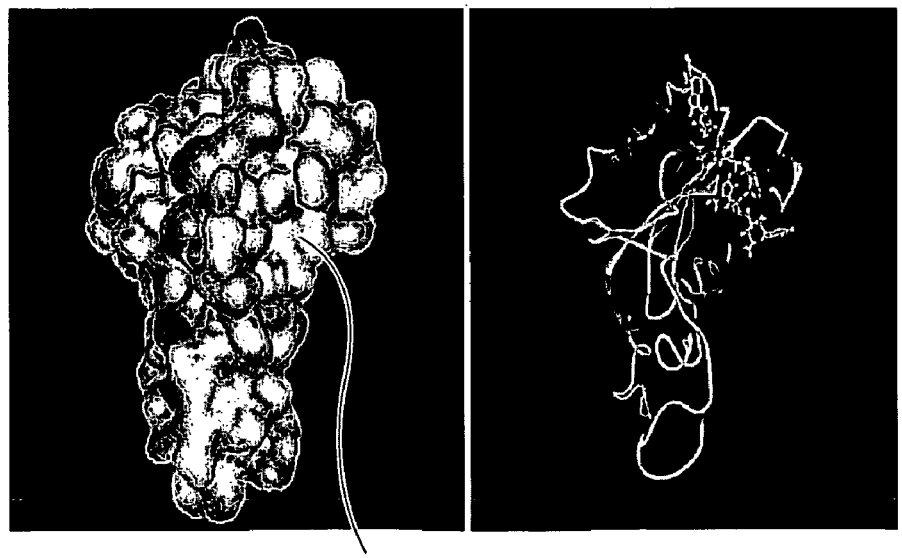
FIG. 9 shows the electrostatic potential surface and the conformation obtained by simulation of R147H mutant diaphorase.
Figure 10:
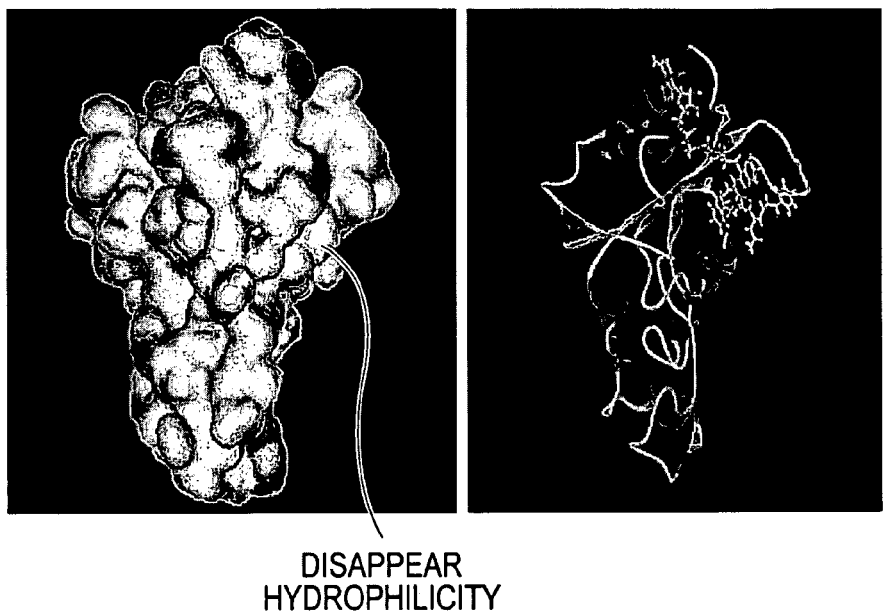
FIG. 10 shows the electrostatic potential surface and the conformation obtained by simulation of G122D mutant diaphorase.

FIGS. 8 to 10 are each a photograph, as an alternative to the drawing, showing the results of structure analysis on the basis of an electrostatic potential surface.

FIG. 8 shows the electrostatic potential surface and the conformation obtained by simulation of wild-type diaphorase. FIG. 9 shows the electrostatic potential surface and the conformation obtained by simulation of R147H mutant diaphorase. FIG. 10 shows the electrostatic potential surface and the conformation obtained by simulation of G122D mutant diaphorase. In each of FIGS. 8 to 10, the left figure is a conformational view showing the electrostatic potential surface. Furthermore, in each of the figures, the term "HYDROPHILIC" indicates a hydrophilic portion, and "DISAPPEAR HYDROPHILICITY" indicates a hydrophobic portion.

As shown in FIG. 8, the vicinity of the flavin-binding site in the wild-type diaphorase is substantially hydrophobic. However, a hydrophilic portion is partly present. In contrast, the hydrophilic portion disappears in the mutant diaphorase.

ANQ, which is a substrate of diaphorase, is a hydrophobic agent. Thus, the above-described results suggest that in the conformation of diaphorase, since the structure in the vicinity of the coenzyme-binding site is changed to be hydrophobic, the interaction with ANQ increases to improve the enzyme activity of diaphorase. That is, the results suggest that the enzyme activity of the mutant protein having a modified structure in which hydrophobicity in the vicinity of the coenzyme-binding site in the conformation is higher than that of the wild-type protein is higher than that of the wild-type diaphorase.

Figure 11:
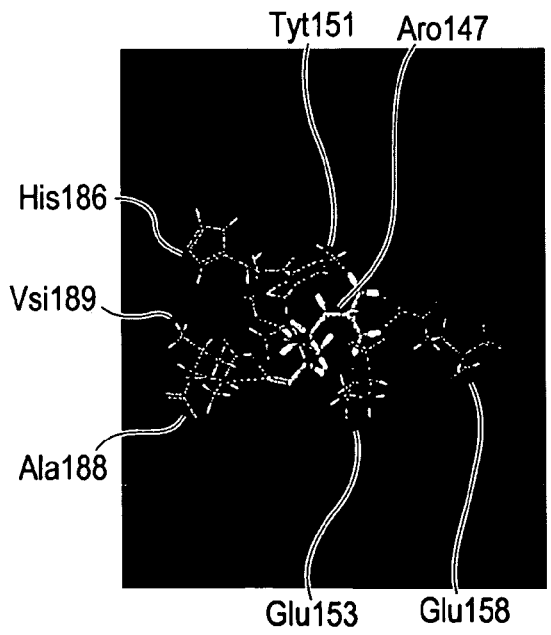
FIG. 11 shows conformational diagrams illustrating hydrogen bonds obtained by simulation of wild-type diaphorase and R147H mutant diaphorase.
Figure 11:
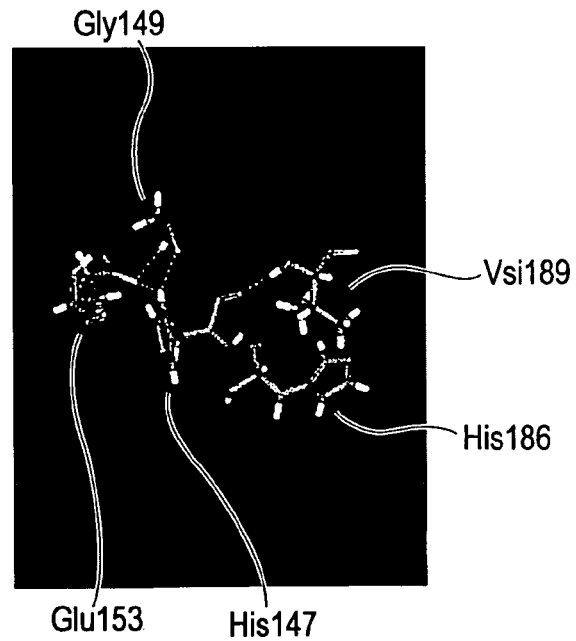
Figure 12:
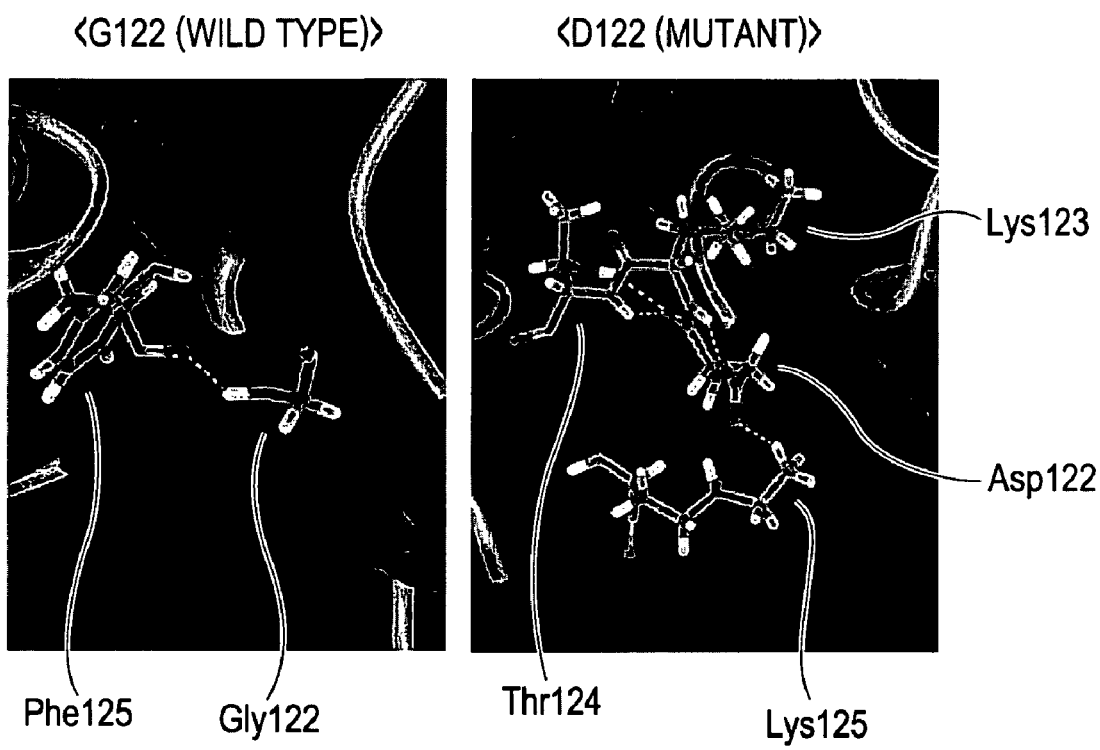
FIG. 12 shows conformational diagrams illustrating hydrogen bonds obtained by simulation of wild-type diaphorase and G122D mutant diaphorase.

FIGS. 11 and 12 are each a photograph, as an alternative to the drawing, showing hydrogen bonds.

FIG. 11 shows conformational diagrams illustrating hydrogen bonds obtained by simulation of wild-type diaphorase and R147H mutant diaphorase. FIG. 12 shows conformational diagrams illustrating hydrogen bonds obtained by simulation of wild-type diaphorase and G122D mutant diaphorase. In each of the figures, the left conformational diagram represents the hydrogen bonds in the wild-type diaphorase, and the right conformational diagram represents the hydrogen bonds in the mutant diaphorase.

As shown in FIGS. 11 and 12, the results of the simulation demonstrated that the number of hydrogen bonds in R147H mutant diaphorase decreased, and the number of hydrogen bonds in G122D mutant diaphorase increased.

The results of the above-described thermostability analysis demonstrated that the thermostability of R147H mutant diaphorase decreased, whereas the thermostability of G122D mutant slightly increased.

The results suggest findings about the thermostability of diaphorase described below.

In the case of R147H mutant diaphorase, the vicinity of the FAD-binding site is modified. The modification reduces the number of hydrogen bonds in the modified region, thus degrading thermostability.

In the case of G122D mutant diaphorase, although the number of hydrogen bonds increases, the modification is not close to the FAD-binding site; hence, thermostability is not so improved. However, G122 is located at a position at which three α-helices in the conformation of diaphorase gather; hence, the increase in the number of hydrogen bonds affects the vicinity of the FAD-binding site via the helices, thereby thermostability increases to some extent.

In summary, the results suggest that the modification for preventing a change in conformation due to the coenzyme (FAD) can improve the thermostability of diaphorase. That is, the results suggest that the thermostability of the mutant protein having a modified structure capable of preventing a change in conformation due to the coenzyme is higher than that of the wild-type diaphorase.

Specifically, with respect to the conformation of diaphorase, the results suggest that the modification such that the number of hydrogen bonds increases in the vicinity of the FAD-binding site; or the modification such that a change in conformation in the vicinity of the FAD-binding site is prevented improves the thermostability of diaphorase.

Figure 13:
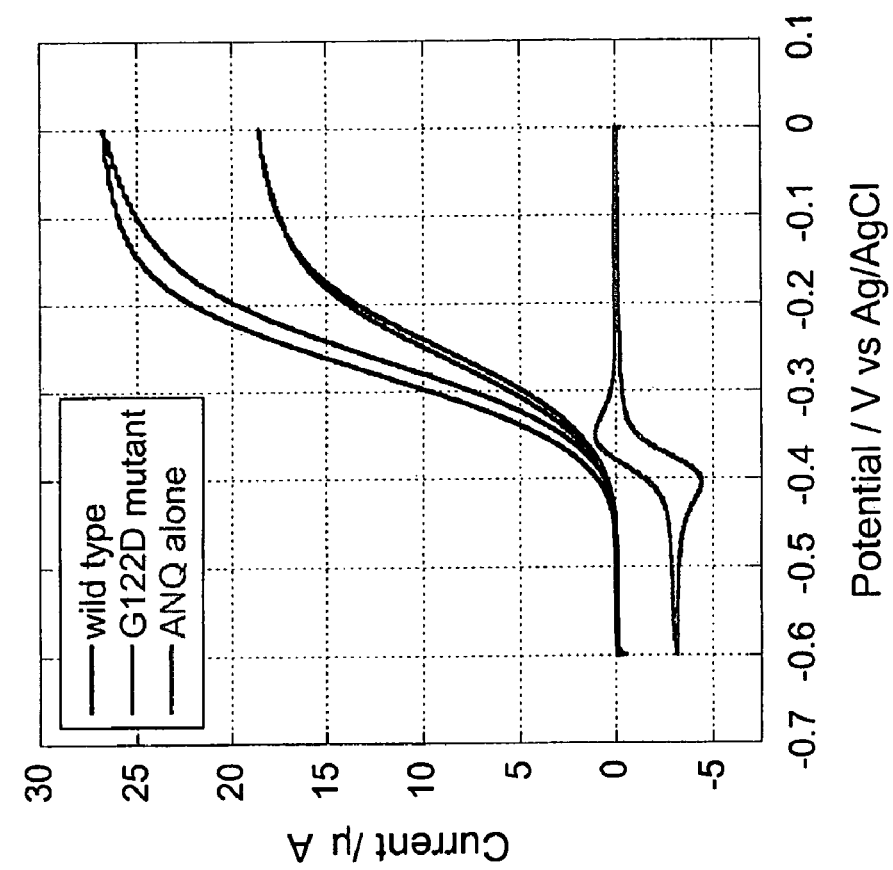
FIG. 13 shows cyclic voltammograms of the redox reaction of ANQ catalyzed by wild type DI and G122D mutant.

The effect of this mutation has been considered electrochemically. FIG. 13 shows the cyclic voltammograms of the redox reaction of ANQ catalyzed by wild type DI (dashed line) and G122D mutant (solid line) at 5 mVs$^{-1}$ scan rate in 0.1 M potassium phosphate buffer (pH 7.8): with GC electrode at [DI]=0.1 µM, [ANQ]=0.4 mM, [NADH]=20 mM.

The current for electrocatalysis by G122D at 0 V is about 1.5 times higher than that by wild type. This result shows that our biofuel cell can be driven by lower amount of ANQ by using G122D mutant.

The effect of mutation of diaphorase practically immobilized on an electrode with poly-L-lysine (PLL) and glutaraldehyde (GA) was evaluated as the following experimentations.

Experimental Procedure

An electrode on which diaphorase was immobilized was produced as follows. A 20 mM NADH solution in a 100 mM potassium phosphate buffer (pH=7.8) was sufficiently subjected to bubbling with argon gas. CV measurement (10 mV/s, −0.6 V to 0.4 V) was performed while ANQ dissolved in dimethyl sulfoxide (DMSO) was gradually added to increase the concentration of ANQ from 0 to 1.8 mM. Production of Electrode Having Diaphorase Immobilized is as follows.

First, various solutions were prepared as follows. A 100 mM sodium dihydrogenphosphate ($NaH_2PO_4$) buffer (I.S.=0.3, pH=8.0) was used as a buffer for the preparation of the solutions.

Diaphorase Buffer (1)

Wild-type diaphorase (DI) or a diaphorase mutant (G122D mutant) was dissolved in 100 µL of the 100 mM sodium dihydrogenphosphate buffer to prepare a diaphorase buffer (1) having a diaphorase concentration of 25 ng/µL (quantified under the conditions in which the molar extinction coefficient of diaphorase was set at 12,000 at 465 nm, and the molecular weight was set at 30,000).

Aqueous Solution of PLL (2)

An appropriate amount of poly-L-lysine hydrobromate (PLL) (P-1524, Mw=513K, manufactured by Sigma-Aldrich Corporation) was dissolved in deionized water to prepare an aqueous solution of 2.0% by weight PLL (2).

Aqueous Solution of GA (3)

An appropriate amount of glutaraldehyde (GA) (071-02031, 10% aqueous solution, manufactured by Wako Pure Chemical Industries, Ltd.) was dissolved in deionized water to prepare an aqueous solution of 0.125% by weight GA (3).

The resulting solutions (1) to (3) were mixed in amounts of diaphorase buffer (1): 2.0 µL, aqueous solution of PLL (2): 3.0 µL and aqueous solution of GA (3): 3.0 µL. The resulting mixture was applied onto only a 3-mm-diameter-electrode section of a glassy carbon electrode having a diameter of 6 mm (manufactured by BAS Inc., the electrode section being covered with a plastic section having a thickness of 1.5 mm) with a micropipette and then appropriately dried to form an electrode having diaphorase immobilized thereon.

Figure 14:
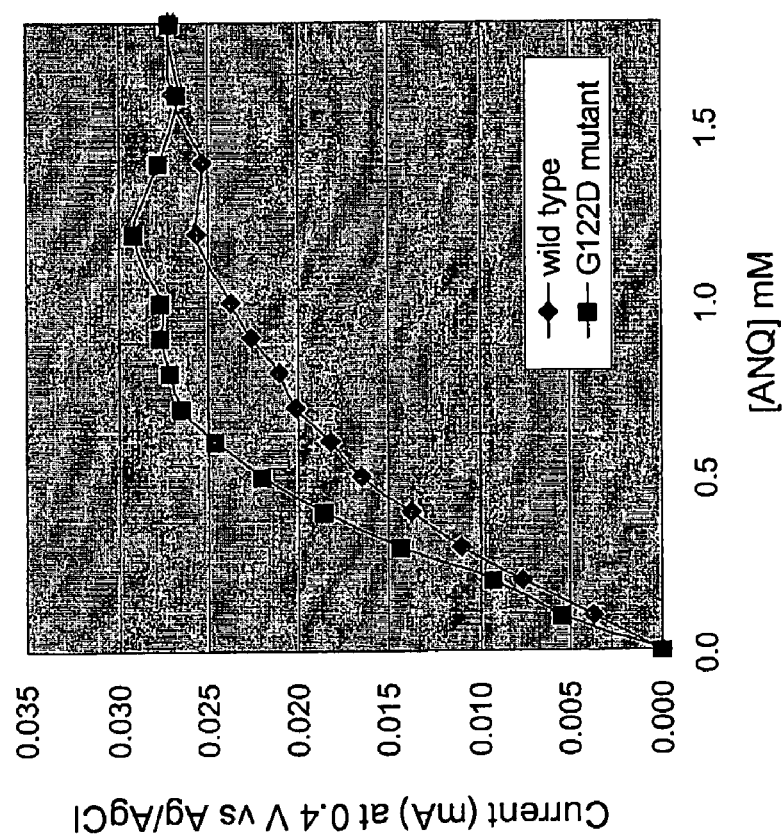
FIG. 14 shows catalyzed Current of DI-immobilized electrode with DI on GC electrode.

FIG. 14 shows cyclic voltammograms of wild-type diaphorase (DI) 50 ng and the diaphorase mutant (G122D mutant) on GC electrode at [NADH]=20 mM in 0.1 M potassium phosphate buffer (pH 7.8). FIG. 14 depicting the currents at 0.4 V in these cyclic voltammograms at different ANQ concentrations ranging from 0 to 1.8 mM in respective solutions. FIG. 14 shows that at low ANQ concentrations, the current in the case of using the G122D mutant was larger than that in the case of using wild-type DI.

Figure 15:
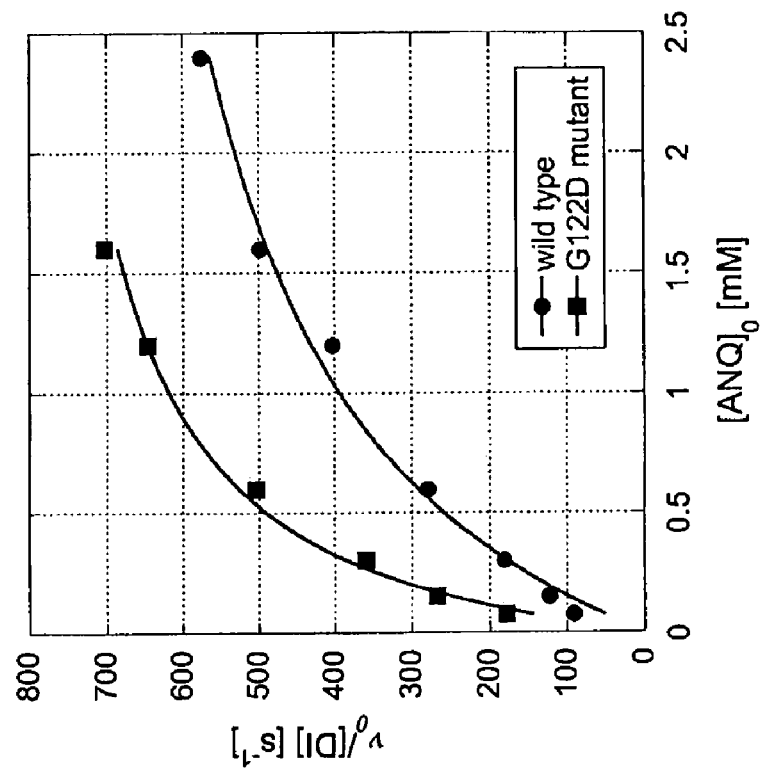
FIG. 15 shows effect of G122D mutation in Solution.

FIG. 15 shows kinetic analyses at [DI]=2.0 nM, [NADH]=40 mM in 0.1 M sodium phosphate buffer (pH 8.0).

As shown in FIG. 15, the diaphorase mutant (G122D mutant) had a $K_M$ value of about ⅓ that of wild-type diaphorase (DI) in the solution. That is, the G122D mutant had an increased affinity for ANQ serving as a substrate, thereby achieving a large current at low ANQ concentrations also in the case of using the G122D mutant practically immobilized on the electrode.

Figure 16:
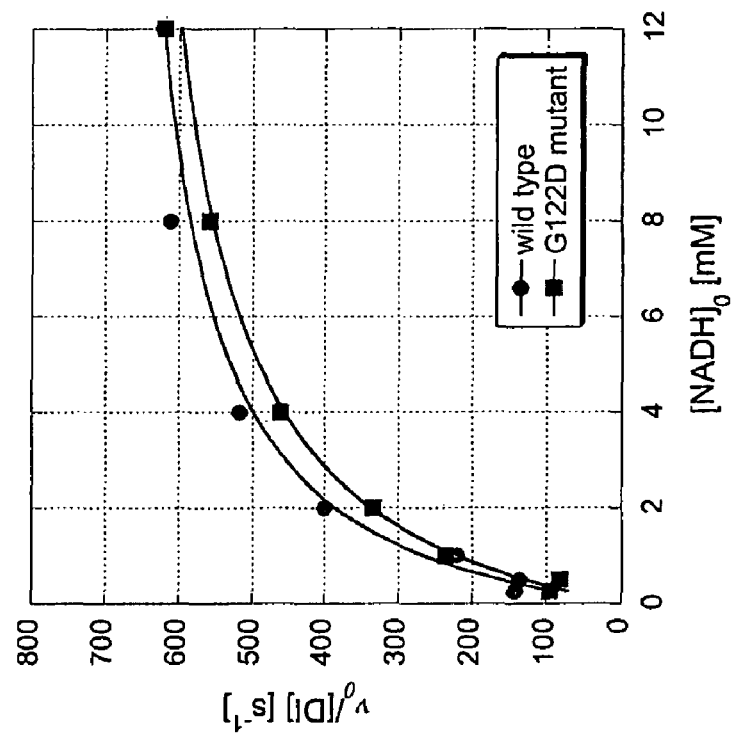
FIG. 16 shows catalyzed current of DI-immobilized electrode with DI on GC electrode.

FIG. 16 shows catalyzed current of DI-immobilized electrode with DI 50 ng on GC electrode at [NADH]=20 mM in 0.1 M potassium phosphate buffer (pH 7.8).

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An isolated mutant diaphorase protein comprising the amino acid sequence of SEQ ID NO: 2, wherein the mutant diaphorase protein has enzyme activity of 245 or more.

* * * * *

SEQUENCE LISTING

<160> NUMBER OF SEQ ID NOS: 60

<210> SEQ ID NO 1
<211> LENGTH: 211
<212> TYPE: PRT
<213> ORGANISM: Bacillus stearothermophilus

<400> SEQUENCE: 1

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Ala Gly Lys Thr Phe Lys Tyr Thr
        115                 120                 125

Glu Gln Gly Pro Val Gly Leu Leu Thr Asp Lys Lys Ala Leu His Ile
    130                 135                 140

Gln Ala Arg Gly Gly Phe Tyr Ser Glu Gly Pro Ala Ala Glu Met Glu
145                 150                 155                 160

Met Gly His Arg Tyr Leu Ser Val Ile Met Gln Phe Phe Gly Val Pro
                165                 170                 175

Ser Phe Glu Gly Leu Phe Val Glu Gly His Ala Ala Val Pro Glu Lys
            180                 185                 190

Ala Glu Glu Ile Lys Ala Asn Ala Ile Ala Arg Ala Lys Asp Leu Ala
        195                 200                 205

His Thr Phe
    210

<210> SEQ ID NO 2
<211> LENGTH: 211
<212> TYPE: PRT
<213> ORGANISM: artificial
<220> FEATURE:
<223> OTHER INFORMATION: mutant diaphorase with K139N/A187E
      substitutions

<400> SEQUENCE: 2

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

```
Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Ala Gly Lys Thr Phe Lys Tyr Thr
            115                 120                 125

Glu Gln Gly Pro Val Gly Leu Leu Thr Asp Asn Lys Ala Leu His Ile
            130                 135                 140

Gln Ala Arg Gly Gly Phe Tyr Ser Glu Gly Pro Ala Ala Glu Met Glu
145                 150                 155                 160

Met Gly His Arg Tyr Leu Ser Val Ile Met Gln Phe Phe Gly Val Pro
                165                 170                 175

Ser Phe Glu Gly Leu Phe Val Glu Gly His Glu Ala Val Pro Glu Lys
            180                 185                 190

Ala Glu Glu Ile Lys Ala Asn Ala Ile Ala Arg Ala Lys Asp Leu Ala
            195                 200                 205

His Thr Phe
    210

<210> SEQ ID NO 3
<211> LENGTH: 211
<212> TYPE: PRT
<213> ORGANISM: artificial
<220> FEATURE:
<223> OTHER INFORMATION: mutant diaphorase with F105L substitution

<400> SEQUENCE: 3

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
            35                  40                  45

Ile Pro Glu Ile Asp Val Asp Val Phe Ser Gly Trp Gly Lys Leu Arg
50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Leu Ser Phe Pro Pro Val Leu Lys
            100                 105                 110

Ala Tyr Ile Asp Ala Val Ala Val Ala Gly Lys Thr Phe Lys Tyr Thr
            115                 120                 125

Glu Gln Gly Pro Val Gly Leu Leu Thr Asp Lys Lys Ala Leu His Ile
            130                 135                 140

Gln Ala Arg Gly Gly Phe Tyr Ser Glu Gly Pro Ala Ala Glu Met Glu
145                 150                 155                 160

Met Gly His Arg Tyr Leu Ser Val Ile Met Gln Phe Phe Gly Val Pro
                165                 170                 175

Ser Phe Glu Gly Leu Phe Val Glu Gly His Ala Ala Val Pro Glu Lys
            180                 185                 190

Ala Glu Glu Ile Lys Ala Asn Ala Ile Ala Arg Ala Lys Asp Leu Ala
            195                 200                 205

His Thr Phe
    210
```

<210> SEQ ID NO 4
<211> LENGTH: 211
<212> TYPE: PRT
<213> ORGANISM: artificial
<220> FEATURE:
<223> OTHER INFORMATION: mutant diaphorase with G122D substitution

<400> SEQUENCE: 4

```
Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Asp Lys Thr Phe Lys Tyr Thr
        115                 120                 125

Glu Gln Gly Pro Val Gly Leu Leu Thr Asp Lys Lys Ala Leu His Ile
    130                 135                 140

Gln Ala Arg Gly Gly Phe Tyr Ser Glu Gly Pro Ala Ala Glu Met Glu
145                 150                 155                 160

Met Gly His Arg Tyr Leu Ser Val Ile Met Gln Phe Phe Gly Val Pro
                165                 170                 175

Ser Phe Glu Gly Leu Phe Val Glu Gly His Ala Ala Val Pro Glu Lys
            180                 185                 190

Ala Glu Glu Ile Lys Ala Asn Ala Ile Ala Arg Ala Lys Asp Leu Ala
        195                 200                 205

His Thr Phe
    210
```

<210> SEQ ID NO 5
<211> LENGTH: 211
<212> TYPE: PRT
<213> ORGANISM: artificial
<220> FEATURE:
<223> OTHER INFORMATION: mutant diaphorase with G131E substitution

<400> SEQUENCE: 5

```
Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
```

```
                    85                  90                  95
Val Phe Val Thr Pro Met Trp Asn Phe Ser Phe Pro Val Leu Lys
                100                 105                 110
Ala Tyr Ile Asp Ala Val Ala Val Ala Gly Lys Thr Phe Lys Tyr Thr
                115                 120                 125
Glu Gln Glu Pro Val Gly Leu Leu Thr Asp Lys Lys Ala Leu His Ile
                130                 135                 140
Gln Ala Arg Gly Gly Phe Tyr Ser Glu Gly Pro Ala Ala Glu Met Glu
145                 150                 155                 160
Met Gly His Arg Tyr Leu Ser Val Ile Met Gln Phe Phe Gly Val Pro
                165                 170                 175
Ser Phe Glu Gly Leu Phe Val Glu Gly His Ala Ala Val Pro Glu Lys
                180                 185                 190
Ala Glu Glu Ile Lys Ala Asn Ala Ile Ala Arg Ala Lys Asp Leu Ala
                195                 200                 205
His Thr Phe
     210

<210> SEQ ID NO 6
<211> LENGTH: 211
<212> TYPE: PRT
<213> ORGANISM: artificial
<220> FEATURE:
<223> OTHER INFORMATION: mutant diaphorase with A146G substitution

<400> SEQUENCE: 6

Met Thr Asn Val Leu Tyr Ile Thr Ala His Pro His Asp Asp Thr Gln
1               5                   10                  15
Ser Tyr Ser Met Ala Val Gly Lys Ala Phe Ile Asp Thr Tyr Lys Gln
                20                  25                  30
Val His Pro Asp His Glu Val Ile His Leu Asp Leu Tyr Lys Glu Tyr
                35                  40                  45
Ile Pro Glu Ile Asp Val Asp Val Phe Ser Gly Trp Gly Lys Leu Arg
50                  55                  60
Ser Gly Lys Ser Phe Glu Glu Leu Ser Asp Glu Glu Lys Ala Lys Val
65                  70                  75                  80
Gly Arg Met Asn Glu Leu Cys Glu Gln Phe Ile Ser Ala Asp Lys Tyr
                85                  90                  95
Val Phe Val Thr Pro Met Trp Asn Phe Ser Phe Pro Val Leu Lys
                100                 105                 110
Ala Tyr Ile Asp Ala Val Ala Val Ala Gly Lys Thr Phe Lys Tyr Thr
                115                 120                 125
Glu Gln Gly Pro Val Gly Leu Leu Thr Asp Lys Lys Ala Leu His Ile
                130                 135                 140
Gln Gly Arg Gly Gly Phe Tyr Ser Glu Gly Pro Ala Ala Glu Met Glu
145                 150                 155                 160
Met Gly His Arg Tyr Leu Ser Val Ile Met Gln Phe Phe Gly Val Pro
                165                 170                 175
Ser Phe Glu Gly Leu Phe Val Glu Gly His Ala Ala Val Pro Glu Lys
                180                 185                 190
Ala Glu Glu Ile Lys Ala Asn Ala Ile Ala Arg Ala Lys Asp Leu Ala
                195                 200                 205
His Thr Phe
     210
```

```
<210> SEQ ID NO 7
<211> LENGTH: 211
<212> TYPE: PRT
<213> ORGANISM: artificial
<220> FEATURE:
<223> OTHER INFORMATION: mutant diaphorase with R147H substitution

<400> SEQUENCE: 7

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Ala Gly Lys Thr Phe Lys Tyr Thr
        115                 120                 125

Glu Gln Gly Pro Val Gly Leu Leu Thr Asp Lys Lys Ala Leu His Ile
    130                 135                 140

Gln Ala His Gly Gly Phe Tyr Ser Glu Gly Pro Ala Ala Glu Met Glu
145                 150                 155                 160

Met Gly His Arg Tyr Leu Ser Val Ile Met Gln Phe Phe Gly Val Pro
                165                 170                 175

Ser Phe Glu Gly Leu Phe Val Glu Gly His Ala Ala Val Pro Glu Lys
            180                 185                 190

Ala Glu Glu Ile Lys Ala Asn Ala Ile Ala Arg Ala Lys Asp Leu Ala
        195                 200                 205

His Thr Phe
    210

<210> SEQ ID NO 8
<211> LENGTH: 211
<212> TYPE: PRT
<213> ORGANISM: artificial
<220> FEATURE:
<223> OTHER INFORMATION: mutant diaphorase with H34Q substitution

<400> SEQUENCE: 8

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val Gln Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95
```

-continued

```
Val Phe Val Thr Pro Met Trp Asn Phe Ser Phe Pro Pro Val Leu Lys
            100                 105                 110

Ala Tyr Ile Asp Ala Val Ala Val Ala Gly Lys Thr Phe Lys Tyr Thr
            115                 120                 125

Glu Gln Gly Pro Val Gly Leu Leu Thr Asp Lys Lys Ala Leu His Ile
            130                 135                 140

Gln Ala Arg Gly Gly Phe Tyr Ser Glu Gly Pro Ala Ala Glu Met Glu
145                 150                 155                 160

Met Gly His Arg Tyr Leu Ser Val Ile Met Gln Phe Gly Val Pro
                165                 170                 175

Ser Phe Glu Gly Leu Phe Val Glu Gly His Ala Ala Val Pro Glu Lys
            180                 185                 190

Ala Glu Glu Ile Lys Ala Asn Ala Ile Ala Arg Ala Lys Asp Leu Ala
            195                 200                 205

His Thr Phe
    210

<210> SEQ ID NO 9
<211> LENGTH: 211
<212> TYPE: PRT
<213> ORGANISM: artificial
<220> FEATURE:
<223> OTHER INFORMATION: mutant diaphorase with F105H substitution

<400> SEQUENCE: 9

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn His Ser Phe Pro Pro Val Leu Lys
            100                 105                 110

Ala Tyr Ile Asp Ala Val Ala Val Ala Gly Lys Thr Phe Lys Tyr Thr
            115                 120                 125

Glu Gln Gly Pro Val Gly Leu Leu Thr Asp Lys Lys Ala Leu His Ile
            130                 135                 140

Gln Ala Arg Gly Gly Phe Tyr Ser Glu Gly Pro Ala Ala Glu Met Glu
145                 150                 155                 160

Met Gly His Arg Tyr Leu Ser Val Ile Met Gln Phe Gly Val Pro
                165                 170                 175

Ser Phe Glu Gly Leu Phe Val Glu Gly His Ala Ala Val Pro Glu Lys
            180                 185                 190

Ala Glu Glu Ile Lys Ala Asn Ala Ile Ala Arg Ala Lys Asp Leu Ala
            195                 200                 205

His Thr Phe
    210

<210> SEQ ID NO 10
<211> LENGTH: 211
```

```
<212> TYPE: PRT
<213> ORGANISM: artificial
<220> FEATURE:
<223> OTHER INFORMATION: mutant diaphorase with A113E substitution

<400> SEQUENCE: 10

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Glu Tyr Ile Asp Ala Val Ala Val Ala Gly Lys Thr Phe Lys Tyr Thr
        115                 120                 125

Glu Gln Gly Pro Val Gly Leu Leu Thr Asp Lys Lys Ala Leu His Ile
    130                 135                 140

Gln Ala Arg Gly Gly Phe Tyr Ser Glu Gly Pro Ala Ala Glu Met Glu
145                 150                 155                 160

Met Gly His Arg Tyr Leu Ser Val Ile Met Gln Phe Gly Val Pro
                165                 170                 175

Ser Phe Glu Gly Leu Phe Val Glu Gly His Ala Ala Val Pro Glu Lys
            180                 185                 190

Ala Glu Glu Ile Lys Ala Asn Ala Ile Ala Arg Ala Lys Asp Leu Ala
        195                 200                 205

His Thr Phe
    210

<210> SEQ ID NO 11
<211> LENGTH: 211
<212> TYPE: PRT
<213> ORGANISM: artificial
<220> FEATURE:
<223> OTHER INFORMATION: mutant diaphorase with K123E substitution

<400> SEQUENCE: 11

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110
```

```
Ala Tyr Ile Asp Ala Val Ala Val Ala Gly Glu Thr Phe Lys Tyr Thr
            115                 120                 125

Glu Gln Gly Pro Val Gly Leu Leu Thr Asp Lys Lys Ala Leu His Ile
        130                 135                 140

Gln Ala Arg Gly Gly Phe Tyr Ser Glu Gly Pro Ala Ala Glu Met Glu
145                 150                 155                 160

Met Gly His Arg Tyr Leu Ser Val Ile Met Gln Phe Gly Val Pro
                165                 170                 175

Ser Phe Glu Gly Leu Phe Val Glu Gly His Ala Ala Val Pro Glu Lys
            180                 185                 190

Ala Glu Glu Ile Lys Ala Asn Ala Ile Ala Arg Ala Lys Asp Leu Ala
        195                 200                 205

His Thr Phe
    210
```

<210> SEQ ID NO 12
<211> LENGTH: 211
<212> TYPE: PRT
<213> ORGANISM: artificial
<220> FEATURE:
<223> OTHER INFORMATION: mutant diaphorase with K139N substitution

<400> SEQUENCE: 12

```
Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
50                  55                  60

Ser Gly Lys Ser Phe Glu Leu Ser Asp Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Ala Gly Lys Thr Phe Lys Tyr Thr
            115                 120                 125

Glu Gln Gly Pro Val Gly Leu Leu Thr Asp Asn Lys Ala Leu His Ile
        130                 135                 140

Gln Ala Arg Gly Gly Phe Tyr Ser Glu Gly Pro Ala Ala Glu Met Glu
145                 150                 155                 160

Met Gly His Arg Tyr Leu Ser Val Ile Met Gln Phe Gly Val Pro
                165                 170                 175

Ser Phe Glu Gly Leu Phe Val Glu Gly His Ala Ala Val Pro Glu Lys
            180                 185                 190

Ala Glu Glu Ile Lys Ala Asn Ala Ile Ala Arg Ala Lys Asp Leu Ala
        195                 200                 205

His Thr Phe
    210
```

<210> SEQ ID NO 13
<211> LENGTH: 211
<212> TYPE: PRT
<213> ORGANISM: artificial

```
<220> FEATURE:
<223> OTHER INFORMATION: mutant diaphorase with R147S substitution

<400> SEQUENCE: 13

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Ala Gly Lys Thr Phe Lys Tyr Thr
        115                 120                 125

Glu Gln Gly Pro Val Gly Leu Leu Thr Asp Lys Lys Ala Leu His Ile
    130                 135                 140

Gln Ala Ser Gly Gly Phe Tyr Ser Glu Gly Pro Ala Ala Glu Met Glu
145                 150                 155                 160

Met Gly His Arg Tyr Leu Ser Val Ile Met Gln Phe Phe Gly Val Pro
                165                 170                 175

Ser Phe Glu Gly Leu Phe Val Glu Gly His Ala Ala Val Pro Glu Lys
            180                 185                 190

Ala Glu Glu Ile Lys Ala Asn Ala Ile Ala Arg Ala Lys Asp Leu Ala
        195                 200                 205

His Thr Phe
    210

<210> SEQ ID NO 14
<211> LENGTH: 211
<212> TYPE: PRT
<213> ORGANISM: artificial
<220> FEATURE:
<223> OTHER INFORMATION: mutant diaphorase with G149D substitution

<400> SEQUENCE: 14

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Ala Gly Lys Thr Phe Lys Tyr Thr
```

```
                    115                 120                 125
Glu Gln Gly Pro Val Gly Leu Leu Thr Asp Lys Lys Ala Leu His Ile
            130                 135                 140

Gln Ala Arg Gly Asp Phe Tyr Ser Glu Gly Pro Ala Ala Glu Met Glu
145                 150                 155                 160

Met Gly His Arg Tyr Leu Ser Val Ile Met Gln Phe Gly Val Pro
                165                 170                 175

Ser Phe Glu Gly Leu Phe Val Glu Gly His Ala Ala Val Pro Glu Lys
            180                 185                 190

Ala Glu Glu Ile Lys Ala Asn Ala Ile Ala Arg Ala Lys Asp Leu Ala
            195                 200                 205

His Thr Phe
    210

<210> SEQ ID NO 15
<211> LENGTH: 211
<212> TYPE: PRT
<213> ORGANISM: artificial
<220> FEATURE:
<223> OTHER INFORMATION: mutant diaphorase with G154D substitution

<400> SEQUENCE: 15

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Ala Gly Lys Thr Phe Lys Tyr Thr
        115                 120                 125

Glu Gln Gly Pro Val Gly Leu Leu Thr Asp Lys Lys Ala Leu His Ile
    130                 135                 140

Gln Ala Arg Gly Gly Phe Tyr Ser Glu Asp Pro Ala Ala Glu Met Glu
145                 150                 155                 160

Met Gly His Arg Tyr Leu Ser Val Ile Met Gln Phe Gly Val Pro
                165                 170                 175

Ser Phe Glu Gly Leu Phe Val Glu Gly His Ala Ala Val Pro Glu Lys
            180                 185                 190

Ala Glu Glu Ile Lys Ala Asn Ala Ile Ala Arg Ala Lys Asp Leu Ala
            195                 200                 205

His Thr Phe
    210

<210> SEQ ID NO 16
<211> LENGTH: 211
<212> TYPE: PRT
<213> ORGANISM: artificial
<220> FEATURE:
<223> OTHER INFORMATION: mutant diaphorase with A156E substitution
```

<400> SEQUENCE: 16

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Ala Gly Lys Thr Phe Lys Tyr Thr
        115                 120                 125

Glu Gln Gly Pro Val Gly Leu Leu Thr Asp Lys Lys Ala Leu His Ile
    130                 135                 140

Gln Ala Arg Gly Gly Phe Tyr Ser Glu Gly Pro Glu Ala Glu Met Glu
145                 150                 155                 160

Met Gly His Arg Tyr Leu Ser Val Ile Met Gln Phe Gly Val Pro
                165                 170                 175

Ser Phe Glu Gly Leu Phe Val Glu Gly His Ala Ala Val Pro Glu Lys
            180                 185                 190

Ala Glu Glu Ile Lys Ala Asn Ala Ile Ala Arg Ala Lys Asp Leu Ala
        195                 200                 205

His Thr Phe
    210

<210> SEQ ID NO 17
<211> LENGTH: 211
<212> TYPE: PRT
<213> ORGANISM: artificial
<220> FEATURE:
<223> OTHER INFORMATION: mutant diaphorase with M159T substitution

<400> SEQUENCE: 17

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Ala Gly Lys Thr Phe Lys Tyr Thr
        115                 120                 125

-continued

```
Glu Gln Gly Pro Val Gly Leu Leu Thr Asp Lys Lys Ala Leu His Ile
    130                 135                 140

Gln Ala Arg Gly Gly Phe Tyr Ser Glu Gly Pro Ala Ala Glu Thr Glu
145                 150                 155                 160

Met Gly His Arg Tyr Leu Ser Val Ile Met Gln Phe Phe Gly Val Pro
                165                 170                 175

Ser Phe Glu Gly Leu Phe Val Glu Gly His Ala Ala Val Pro Glu Lys
            180                 185                 190

Ala Glu Glu Ile Lys Ala Asn Ala Ile Ala Arg Ala Lys Asp Leu Ala
        195                 200                 205

His Thr Phe
    210

<210> SEQ ID NO 18
<211> LENGTH: 211
<212> TYPE: PRT
<213> ORGANISM: artificial
<220> FEATURE:
<223> OTHER INFORMATION: mutant diaphorase with A187E substitution

<400> SEQUENCE: 18

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Ala Gly Lys Thr Phe Lys Tyr Thr
        115                 120                 125

Glu Gln Gly Pro Val Gly Leu Leu Thr Asp Lys Lys Ala Leu His Ile
    130                 135                 140

Gln Ala Arg Gly Gly Phe Tyr Ser Glu Gly Pro Ala Ala Glu Met Glu
145                 150                 155                 160

Met Gly His Arg Tyr Leu Ser Val Ile Met Gln Phe Phe Gly Val Pro
                165                 170                 175

Ser Phe Glu Gly Leu Phe Val Glu Gly His Glu Ala Val Pro Glu Lys
            180                 185                 190

Ala Glu Glu Ile Lys Ala Asn Ala Ile Ala Arg Ala Lys Asp Leu Ala
        195                 200                 205

His Thr Phe
    210

<210> SEQ ID NO 19
<211> LENGTH: 211
<212> TYPE: PRT
<213> ORGANISM: artificial
<220> FEATURE:
<223> OTHER INFORMATION: mutant diaphorase with A187T substitution

<400> SEQUENCE: 19
```

```
Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Ala Gly Lys Thr Phe Lys Tyr Thr
        115                 120                 125

Glu Gln Gly Pro Val Gly Leu Leu Thr Asp Lys Lys Ala Leu His Ile
130                 135                 140

Gln Ala Arg Gly Gly Phe Tyr Ser Glu Gly Pro Ala Ala Glu Met Glu
145                 150                 155                 160

Met Gly His Arg Tyr Leu Ser Val Ile Met Gln Phe Phe Gly Val Pro
                165                 170                 175

Ser Phe Glu Gly Leu Phe Val Glu Gly His Thr Ala Val Pro Glu Lys
            180                 185                 190

Ala Glu Glu Ile Lys Ala Asn Ala Ile Ala Arg Ala Lys Asp Leu Ala
        195                 200                 205

His Thr Phe
    210
```

<210> SEQ ID NO 20
<211> LENGTH: 211
<212> TYPE: PRT
<213> ORGANISM: artificial
<220> FEATURE:
<223> OTHER INFORMATION: mutant diaphorase with A187V substitution

<400> SEQUENCE: 20

```
Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Ala Gly Lys Thr Phe Lys Tyr Thr
        115                 120                 125

Glu Gln Gly Pro Val Gly Leu Leu Thr Asp Lys Lys Ala Leu His Ile
130                 135                 140
```

```
Gln Ala Arg Gly Gly Phe Tyr Ser Glu Gly Pro Ala Ala Glu Met Glu
145                 150                 155                 160

Met Gly His Arg Tyr Leu Ser Val Ile Met Gln Phe Gly Val Pro
                165                 170                 175

Ser Phe Glu Gly Leu Phe Val Glu Gly His Val Ala Val Pro Glu Lys
                180                 185                 190

Ala Glu Glu Ile Lys Ala Asn Ala Ile Ala Arg Ala Lys Asp Leu Ala
                195                 200                 205

His Thr Phe
        210

<210> SEQ ID NO 21
<211> LENGTH: 211
<212> TYPE: PRT
<213> ORGANISM: artificial
<220> FEATURE:
<223> OTHER INFORMATION: mutant diaphorase with R64H/A146T substitutions

<400> SEQUENCE: 21

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
                20                  25                  30

Val His Pro Asp His Glu Val Ile His Leu Asp Leu Tyr Lys Glu Tyr
            35                  40                  45

Ile Pro Glu Ile Asp Val Asp Val Phe Ser Gly Trp Gly Lys Leu His
        50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
                100                 105                 110

Ala Tyr Ile Asp Ala Val Ala Val Ala Gly Lys Thr Phe Lys Tyr Thr
                115                 120                 125

Glu Gln Gly Pro Val Gly Leu Leu Thr Asp Lys Lys Ala Leu His Ile
130                 135                 140

Gln Thr Arg Gly Gly Phe Tyr Ser Glu Gly Pro Ala Ala Glu Met Glu
145                 150                 155                 160

Met Gly His Arg Tyr Leu Ser Val Ile Met Gln Phe Gly Val Pro
                165                 170                 175

Ser Phe Glu Gly Leu Phe Val Glu Gly His Ala Ala Val Pro Glu Lys
                180                 185                 190

Ala Glu Glu Ile Lys Ala Asn Ala Ile Ala Arg Ala Lys Asp Leu Ala
                195                 200                 205

His Thr Phe
        210

<210> SEQ ID NO 22
<211> LENGTH: 211
<212> TYPE: PRT
<213> ORGANISM: artificial
<220> FEATURE:
<223> OTHER INFORMATION: mutant diaphorase with E85D/R147H substitutions

<400> SEQUENCE: 22

Met Thr Asn Val Leu Tyr Ile Thr Ala His Pro His Asp Asp Thr Gln
```

```
                 1               5               10              15

Ser Tyr Ser Met Ala Val Gly Lys Ala Phe Ile Asp Thr Tyr Lys Gln
                    20              25              30

Val His Pro Asp His Glu Val Ile His Leu Asp Leu Tyr Lys Glu Tyr
                    35              40              45

Ile Pro Glu Ile Asp Val Asp Val Phe Ser Gly Trp Gly Lys Leu Arg
        50              55              60

Ser Gly Lys Ser Phe Glu Glu Leu Ser Asp Glu Glu Lys Ala Lys Val
65                      70              75              80

Gly Arg Met Asn Asp Leu Cys Glu Gln Phe Ile Ser Ala Asp Lys Tyr
                        85              90              95

Val Phe Val Thr Pro Met Trp Asn Phe Ser Phe Pro Pro Val Leu Lys
                    100             105             110

Ala Tyr Ile Asp Ala Val Ala Val Ala Gly Lys Thr Phe Lys Tyr Thr
                    115             120             125

Glu Gln Gly Pro Val Gly Leu Leu Thr Asp Lys Lys Ala Leu His Ile
                    130             135             140

Gln Ala His Gly Gly Phe Tyr Ser Glu Gly Pro Ala Ala Glu Met Glu
145                     150             155             160

Met Gly His Arg Tyr Leu Ser Val Ile Met Gln Phe Phe Gly Val Pro
                    165             170             175

Ser Phe Glu Gly Leu Phe Val Glu Gly His Ala Ala Val Pro Glu Lys
                    180             185             190

Ala Glu Glu Ile Lys Ala Asn Ala Ile Ala Arg Ala Lys Asp Leu Ala
                    195             200             205

His Thr Phe
        210

<210> SEQ ID NO 23
<211> LENGTH: 211
<212> TYPE: PRT
<213> ORGANISM: artificial
<220> FEATURE:
<223> OTHER INFORMATION: mutant diaphorase with F105L/A187E
      substitutions

<400> SEQUENCE: 23

Met Thr Asn Val Leu Tyr Ile Thr Ala His Pro His Asp Asp Thr Gln
1               5               10              15

Ser Tyr Ser Met Ala Val Gly Lys Ala Phe Ile Asp Thr Tyr Lys Gln
                    20              25              30

Val His Pro Asp His Glu Val Ile His Leu Asp Leu Tyr Lys Glu Tyr
                    35              40              45

Ile Pro Glu Ile Asp Val Asp Val Phe Ser Gly Trp Gly Lys Leu Arg
        50              55              60

Ser Gly Lys Ser Phe Glu Glu Leu Ser Asp Glu Glu Lys Ala Lys Val
65                      70              75              80

Gly Arg Met Asn Glu Leu Cys Glu Gln Phe Ile Ser Ala Asp Lys Tyr
                        85              90              95

Val Phe Val Thr Pro Met Trp Asn Leu Ser Phe Pro Pro Val Leu Lys
                    100             105             110

Ala Tyr Ile Asp Ala Val Ala Val Ala Gly Lys Thr Phe Lys Tyr Thr
                    115             120             125

Glu Gln Gly Pro Val Gly Leu Leu Thr Asp Lys Lys Ala Leu His Ile
                    130             135             140
```

```
Gln Ala Arg Gly Gly Phe Tyr Ser Glu Gly Pro Ala Ala Glu Met Glu
145                 150                 155                 160

Met Gly His Arg Tyr Leu Ser Val Ile Met Gln Phe Phe Gly Val Pro
                165                 170                 175

Ser Phe Glu Gly Leu Phe Val Glu Gly His Ala Val Pro Glu Lys
            180                 185                 190

Ala Glu Glu Ile Lys Ala Asn Ala Ile Ala Arg Ala Lys Asp Leu Ala
            195                 200                 205

His Thr Phe
    210

<210> SEQ ID NO 24
<211> LENGTH: 211
<212> TYPE: PRT
<213> ORGANISM: artificial
<220> FEATURE:
<223> OTHER INFORMATION: mutant diaphorase with A113E/K126N
      substitutions

<400> SEQUENCE: 24

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
                20                  25                  30

Val His Pro Asp His Glu Val Ile His Leu Asp Leu Tyr Lys Glu Tyr
            35                  40                  45

Ile Pro Glu Ile Asp Val Asp Val Phe Ser Gly Trp Gly Lys Leu Arg
50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Glu Tyr Ile Asp Ala Val Ala Val Ala Gly Lys Thr Phe Asn Tyr Thr
        115                 120                 125

Glu Gln Gly Pro Val Gly Leu Leu Thr Asp Lys Lys Ala Leu His Ile
130                 135                 140

Gln Ala Arg Gly Gly Phe Tyr Ser Glu Gly Pro Ala Ala Glu Met Glu
145                 150                 155                 160

Met Gly His Arg Tyr Leu Ser Val Ile Met Gln Phe Phe Gly Val Pro
                165                 170                 175

Ser Phe Glu Gly Leu Phe Val Glu Gly His Ala Val Pro Glu Lys
            180                 185                 190

Ala Glu Glu Ile Lys Ala Asn Ala Ile Ala Arg Ala Lys Asp Leu Ala
            195                 200                 205

His Thr Phe
    210

<210> SEQ ID NO 25
<211> LENGTH: 211
<212> TYPE: PRT
<213> ORGANISM: artificial
<220> FEATURE:
<223> OTHER INFORMATION: mutant diaphorase with Y151H/A187E
      substitutions

<400> SEQUENCE: 25
```

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
            35                  40                  45

Ile Pro Glu Ile Asp Val Asp Val Phe Ser Gly Trp Gly Lys Leu Arg
        50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Ala Gly Lys Thr Phe Lys Tyr Thr
        115                 120                 125

Glu Gln Gly Pro Val Gly Leu Leu Thr Asp Lys Lys Ala Leu His Ile
130                 135                 140

Gln Ala Arg Gly Gly Phe His Ser Glu Gly Pro Ala Ala Glu Met Glu
145                 150                 155                 160

Met Gly His Arg Tyr Leu Ser Val Ile Met Gln Phe Phe Gly Val Pro
                165                 170                 175

Ser Phe Glu Gly Leu Phe Val Glu Gly His Glu Ala Val Pro Glu Lys
            180                 185                 190

Ala Glu Glu Ile Lys Ala Asn Ala Ile Ala Arg Ala Lys Asp Leu Ala
        195                 200                 205

His Thr Phe
    210

<210> SEQ ID NO 26
<211> LENGTH: 211
<212> TYPE: PRT
<213> ORGANISM: artificial
<220> FEATURE:
<223> OTHER INFORMATION: mutant diaphorase with G122D/A187E
      substitutions

<400> SEQUENCE: 26

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
            35                  40                  45

Ile Pro Glu Ile Asp Val Asp Val Phe Ser Gly Trp Gly Lys Leu Arg
        50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Ala Asp Lys Thr Phe Lys Tyr Thr
        115                 120                 125

Glu Gln Gly Pro Val Gly Leu Leu Thr Asp Lys Lys Ala Leu His Ile
130                 135                 140

```
Gln Ala Arg Gly Gly Phe Tyr Ser Glu Gly Pro Ala Ala Glu Met Glu
145                 150                 155                 160

Met Gly His Arg Tyr Leu Ser Val Ile Met Gln Phe Gly Val Pro
            165                 170                 175

Ser Phe Glu Gly Leu Phe Val Glu Gly His Glu Ala Val Pro Glu Lys
            180                 185                 190

Ala Glu Glu Ile Lys Ala Asn Ala Ile Ala Arg Ala Lys Asp Leu Ala
            195                 200                 205

His Thr Phe
    210

<210> SEQ ID NO 27
<211> LENGTH: 211
<212> TYPE: PRT
<213> ORGANISM: artificial
<220> FEATURE:
<223> OTHER INFORMATION: mutant diaphorase with G149D/A187E
      substitutions

<400> SEQUENCE: 27

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
            35                  40                  45

Ile Pro Glu Ile Asp Val Asp Val Phe Ser Gly Trp Gly Lys Leu Arg
50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Ala Gly Lys Thr Phe Lys Tyr Thr
            115                 120                 125

Glu Gln Gly Pro Val Gly Leu Leu Thr Asp Lys Lys Ala Leu His Ile
130                 135                 140

Gln Ala Arg Gly Asp Phe Tyr Ser Glu Gly Pro Ala Ala Glu Met Glu
145                 150                 155                 160

Met Gly His Arg Tyr Leu Ser Val Ile Met Gln Phe Gly Val Pro
            165                 170                 175

Ser Phe Glu Gly Leu Phe Val Glu Gly His Glu Ala Val Pro Glu Lys
            180                 185                 190

Ala Glu Glu Ile Lys Ala Asn Ala Ile Ala Arg Ala Lys Asp Leu Ala
            195                 200                 205

His Thr Phe
    210

<210> SEQ ID NO 28
<211> LENGTH: 211
<212> TYPE: PRT
<213> ORGANISM: artificial
<220> FEATURE:
<223> OTHER INFORMATION: mutant diaphorase with G149S/A187E/L207W
      substitutions

<400> SEQUENCE: 28
```

```
Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65              70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Ala Gly Lys Thr Phe Lys Tyr Thr
        115                 120                 125

Glu Gln Gly Pro Val Gly Leu Leu Thr Asp Lys Lys Ala Leu His Ile
130                 135                 140

Gln Ala Arg Gly Ser Phe Tyr Ser Glu Gly Pro Ala Ala Glu Met Glu
145                 150                 155                 160

Met Gly His Arg Tyr Leu Ser Val Ile Met Gln Phe Phe Gly Val Pro
                165                 170                 175

Ser Phe Glu Gly Leu Phe Val Glu Gly His Glu Ala Val Pro Glu Lys
            180                 185                 190

Ala Glu Glu Ile Lys Ala Asn Ala Ile Ala Arg Ala Lys Asp Trp Ala
        195                 200                 205

His Thr Phe
    210

<210> SEQ ID NO 29
<211> LENGTH: 211
<212> TYPE: PRT
<213> ORGANISM: artificial
<220> FEATURE:
<223> OTHER INFORMATION: mutant diaphorase with F105L/A187E/L207W
      substitutions

<400> SEQUENCE: 29

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65              70                  75                  80

Gly Arg Met Asn Glu Leu Cys Glu Gln Phe Ile Ser Ala Asp Lys Tyr
                85                  90                  95

Val Phe Val Thr Pro Met Trp Asn Leu Ser Phe Pro Pro Val Leu Lys
            100                 105                 110

Ala Tyr Ile Asp Ala Val Ala Val Ala Gly Lys Thr Phe Lys Tyr Thr
        115                 120                 125

Glu Gln Gly Pro Val Gly Leu Leu Thr Asp Lys Lys Ala Leu His Ile
```

-continued

```
                    130                 135                 140
Gln Ala Arg Gly Gly Phe Tyr Ser Glu Gly Pro Ala Ala Glu Met Glu
145                 150                 155                 160

Met Gly His Arg Tyr Leu Ser Val Ile Met Gln Phe Phe Gly Val Pro
                165                 170                 175

Ser Phe Glu Gly Leu Phe Val Glu Gly His Glu Ala Val Pro Glu Lys
            180                 185                 190

Ala Glu Glu Ile Lys Ala Asn Ala Ile Ala Arg Ala Lys Asp Trp Ala
        195                 200                 205

His Thr Phe
    210

<210> SEQ ID NO 30
<211> LENGTH: 211
<212> TYPE: PRT
<213> ORGANISM: artificial
<220> FEATURE:
<223> OTHER INFORMATION: mutant diaphorase with G66R/F105L/A187E/K192R
      substitutions

<400> SEQUENCE: 30

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
50                  55                  60

Ser Arg Lys Ser Phe Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Leu Ser Phe Pro Pro Val Leu Lys
            100                 105                 110

Ala Tyr Ile Asp Ala Val Ala Val Ala Gly Lys Thr Phe Lys Tyr Thr
        115                 120                 125

Glu Gln Gly Pro Val Gly Leu Leu Thr Asp Lys Lys Ala Leu His Ile
    130                 135                 140

Gln Ala Arg Gly Gly Phe Tyr Ser Glu Gly Pro Ala Ala Glu Met Glu
145                 150                 155                 160

Met Gly His Arg Tyr Leu Ser Val Ile Met Gln Phe Phe Gly Val Pro
                165                 170                 175

Ser Phe Glu Gly Leu Phe Val Glu Gly His Glu Ala Val Pro Glu Arg
            180                 185                 190

Ala Glu Glu Ile Lys Ala Asn Ala Ile Ala Arg Ala Lys Asp Leu Ala
        195                 200                 205

His Thr Phe
    210

<210> SEQ ID NO 31
<211> LENGTH: 211
<212> TYPE: PRT
<213> ORGANISM: artificial
<220> FEATURE:
<223> OTHER INFORMATION: mutant diaphorase with A146G/L207W
      substitutions
```

<400> SEQUENCE: 31

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Ala Gly Lys Thr Phe Lys Tyr Thr
        115                 120                 125

Glu Gln Gly Pro Val Gly Leu Leu Thr Asp Lys Lys Ala Leu His Ile
    130                 135                 140

Gln Gly Arg Gly Gly Phe Tyr Ser Glu Gly Pro Ala Ala Glu Met Glu
145                 150                 155                 160

Met Gly His Arg Tyr Leu Ser Val Ile Met Gln Phe Phe Gly Val Pro
                165                 170                 175

Ser Phe Glu Gly Leu Phe Val Glu Gly His Ala Ala Val Pro Glu Lys
            180                 185                 190

Ala Glu Glu Ile Lys Ala Asn Ala Ile Ala Arg Ala Lys Asp Trp Ala
        195                 200                 205

His Thr Phe
    210

<210> SEQ ID NO 32
<211> LENGTH: 211
<212> TYPE: PRT
<213> ORGANISM: artificial
<220> FEATURE:
<223> OTHER INFORMATION: mutant diaphorase with F105L/A187E/Q171P
      substitutions

<400> SEQUENCE: 32

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Leu Ser Phe Pro Pro Val Leu Lys
            100                 105                 110

Ala Tyr Ile Asp Ala Val Ala Val Ala Gly Lys Thr Phe Lys Tyr Thr
        115                 120                 125

```
Glu Gln Gly Pro Val Gly Leu Leu Thr Asp Lys Lys Ala Leu His Ile
    130                 135                 140

Gln Ala Arg Gly Gly Phe Tyr Ser Glu Gly Pro Ala Ala Glu Met Glu
145                 150                 155                 160

Met Gly His Arg Tyr Leu Ser Val Ile Met Pro Phe Phe Gly Val Pro
                165                 170                 175

Ser Phe Glu Gly Leu Phe Val Glu Gly His Glu Ala Val Pro Glu Lys
                180                 185                 190

Ala Glu Glu Ile Lys Ala Asn Ala Ile Ala Arg Ala Lys Asp Leu Ala
        195                 200                 205

His Thr Phe
    210

<210> SEQ ID NO 33
<211> LENGTH: 211
<212> TYPE: PRT
<213> ORGANISM: artificial
<220> FEATURE:
<223> OTHER INFORMATION: mutant diaphorase with A78E/F105L/A187E
      substitutions

<400> SEQUENCE: 33

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
50                  55                  60

Ser Gly Lys Ser Phe Glu Glu Leu Ser Asp Glu Glu Lys Glu Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Leu Ser Phe Pro Pro Val Leu Lys
            100                 105                 110

Ala Tyr Ile Asp Ala Val Ala Val Ala Gly Lys Thr Phe Lys Tyr Thr
        115                 120                 125

Glu Gln Gly Pro Val Gly Leu Leu Thr Asp Lys Lys Ala Leu His Ile
    130                 135                 140

Gln Ala Arg Gly Gly Phe Tyr Ser Glu Gly Pro Ala Ala Glu Met Glu
145                 150                 155                 160

Met Gly His Arg Tyr Leu Ser Val Ile Met Gln Phe Phe Gly Val Pro
                165                 170                 175

Ser Phe Glu Gly Leu Phe Val Glu Gly His Glu Ala Val Pro Glu Lys
                180                 185                 190

Ala Glu Glu Ile Lys Ala Asn Ala Ile Ala Arg Ala Lys Asp Leu Ala
        195                 200                 205

His Thr Phe
    210

<210> SEQ ID NO 34
<211> LENGTH: 211
<212> TYPE: PRT
<213> ORGANISM: artificial
<220> FEATURE:
<223> OTHER INFORMATION: mutant diaphorase with F105L/K139N/V168L/A187E
      substitutions
```

```
<400> SEQUENCE: 34

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Leu Ser Phe Pro Pro Val Leu Lys
            100                 105                 110

Ala Tyr Ile Asp Ala Val Ala Val Ala Gly Lys Thr Phe Lys Tyr Thr
        115                 120                 125

Glu Gln Gly Pro Val Gly Leu Leu Thr Asp Asn Lys Ala Leu His Ile
    130                 135                 140

Gln Ala Arg Gly Gly Phe Tyr Ser Gly Pro Ala Ala Glu Met Glu
145                 150                 155                 160

Met Gly His Arg Tyr Leu Ser Leu Ile Met Gln Phe Gly Val Pro
                165                 170                 175

Ser Phe Glu Gly Leu Phe Val Glu Gly His Glu Ala Val Pro Glu Lys
            180                 185                 190

Ala Glu Glu Ile Lys Ala Asn Ala Ile Ala Arg Ala Lys Asp Leu Ala
        195                 200                 205

His Thr Phe
    210

<210> SEQ ID NO 35
<211> LENGTH: 211
<212> TYPE: PRT
<213> ORGANISM: artificial
<220> FEATURE:
<223> OTHER INFORMATION: mutant diaphorase with G154D/G180R
      substitutions

<400> SEQUENCE: 35

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Ala Gly Lys Thr Phe Lys Tyr Thr
        115                 120                 125
```

```
Glu Gln Gly Pro Val Gly Leu Leu Thr Asp Lys Lys Ala Leu His Ile
        130                 135                 140

Gln Ala Arg Gly Gly Phe Tyr Ser Glu Asp Pro Ala Ala Glu Met Glu
145                 150                 155                 160

Met Gly His Arg Tyr Leu Ser Val Ile Met Gln Phe Phe Gly Val Pro
                165                 170                 175

Ser Phe Glu Arg Leu Phe Val Glu Gly His Ala Ala Val Pro Glu Lys
            180                 185                 190

Ala Glu Glu Ile Lys Ala Asn Ala Ile Ala Arg Ala Lys Asp Leu Ala
        195                 200                 205

His Thr Phe
    210

<210> SEQ ID NO 36
<211> LENGTH: 211
<212> TYPE: PRT
<213> ORGANISM: artificial
<220> FEATURE:
<223> OTHER INFORMATION: mutant diaphorase with F107I substitution

<400> SEQUENCE: 36

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
50                  55                  60

Ser Gly Lys Ser Phe Glu Glu Leu Ser Asp Glu Gln Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Ile Pro Pro Val Leu Lys
            100                 105                 110

Ala Tyr Ile Asp Ala Val Ala Val Ala Gly Lys Thr Phe Lys Tyr Thr
        115                 120                 125

Glu Gln Gly Pro Val Gly Leu Leu Thr Asp Lys Lys Ala Leu His Ile
        130                 135                 140

Gln Ala Arg Gly Gly Phe Tyr Ser Glu Gly Pro Ala Ala Glu Met Glu
145                 150                 155                 160

Met Gly His Arg Tyr Leu Ser Val Ile Met Gln Phe Phe Gly Val Pro
                165                 170                 175

Ser Phe Glu Gly Leu Phe Val Glu Gly His Ala Ala Val Pro Glu Lys
            180                 185                 190

Ala Glu Glu Ile Lys Ala Asn Ala Ile Ala Arg Ala Lys Asp Leu Ala
        195                 200                 205

His Thr Phe
    210

<210> SEQ ID NO 37
<211> LENGTH: 211
<212> TYPE: PRT
<213> ORGANISM: artificial
<220> FEATURE:
<223> OTHER INFORMATION: mutant diaphorase with G185R substitution
```

<400> SEQUENCE: 37

```
Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Ala Gly Lys Thr Phe Lys Tyr Thr
        115                 120                 125

Glu Gln Gly Pro Val Gly Leu Leu Thr Asp Lys Lys Ala Leu His Ile
130                 135                 140

Gln Ala Arg Gly Gly Phe Tyr Ser Glu Gly Pro Ala Ala Glu Met Glu
145                 150                 155                 160

Met Gly His Arg Tyr Leu Ser Val Ile Met Gln Phe Phe Gly Val Pro
                165                 170                 175

Ser Phe Glu Gly Leu Phe Val Glu Arg His Ala Ala Val Pro Glu Lys
            180                 185                 190

Ala Glu Glu Ile Lys Ala Asn Ala Ile Ala Arg Ala Lys Asp Leu Ala
        195                 200                 205

His Thr Phe
    210
```

<210> SEQ ID NO 38
<211> LENGTH: 211
<212> TYPE: PRT
<213> ORGANISM: artificial
<220> FEATURE:
<223> OTHER INFORMATION: mutant diaphorase with Y151H/G185R substitutions

<400> SEQUENCE: 38

```
Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Ala Gly Lys Thr Phe Lys Tyr Thr
        115                 120                 125
```

```
Glu Gln Gly Pro Val Gly Leu Leu Thr Asp Lys Lys Ala Leu His Ile
    130                 135                 140

Gln Ala Arg Gly Gly Phe His Ser Glu Gly Pro Ala Ala Glu Met Glu
145                 150                 155                 160

Met Gly His Arg Tyr Leu Ser Val Ile Met Gln Phe Phe Gly Val Pro
                165                 170                 175

Ser Phe Glu Gly Leu Phe Val Glu Arg His Ala Ala Val Pro Glu Lys
            180                 185                 190

Ala Glu Glu Ile Lys Ala Asn Ala Ile Ala Arg Ala Lys Asp Leu Ala
        195                 200                 205

His Thr Phe
    210

<210> SEQ ID NO 39
<211> LENGTH: 211
<212> TYPE: PRT
<213> ORGANISM: artificial
<220> FEATURE:
<223> OTHER INFORMATION: mutant diaphorase with G122D/G185R
      substitutions

<400> SEQUENCE: 39

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Ala Asp Lys Thr Phe Lys Tyr Thr
        115                 120                 125

Glu Gln Gly Pro Val Gly Leu Leu Thr Asp Lys Lys Ala Leu His Ile
    130                 135                 140

Gln Ala Arg Gly Gly Phe Tyr Ser Glu Gly Pro Ala Ala Glu Met Glu
145                 150                 155                 160

Met Gly His Arg Tyr Leu Ser Val Ile Met Gln Phe Phe Gly Val Pro
                165                 170                 175

Ser Phe Glu Gly Leu Phe Val Glu Arg His Ala Ala Val Pro Glu Lys
            180                 185                 190

Ala Glu Glu Ile Lys Ala Asn Ala Ile Ala Arg Ala Lys Asp Leu Ala
        195                 200                 205

His Thr Phe
    210

<210> SEQ ID NO 40
<211> LENGTH: 211
<212> TYPE: PRT
<213> ORGANISM: artificial
<220> FEATURE:
<223> OTHER INFORMATION: mutant diaphorase with G149D/G185R
      substitutions
```

<400> SEQUENCE: 40

```
Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Ala Gly Lys Thr Phe Lys Tyr Thr
        115                 120                 125

Glu Gln Gly Pro Val Gly Leu Leu Thr Asp Lys Lys Ala Leu His Ile
    130                 135                 140

Gln Ala Arg Gly Asp Phe Tyr Ser Glu Gly Pro Ala Ala Glu Met Glu
145                 150                 155                 160

Met Gly His Arg Tyr Leu Ser Val Ile Met Gln Phe Gly Val Pro
                165                 170                 175

Ser Phe Glu Gly Leu Phe Val Glu Arg His Ala Ala Val Pro Glu Lys
            180                 185                 190

Ala Glu Glu Ile Lys Ala Asn Ala Ile Ala Arg Ala Lys Asp Leu Ala
        195                 200                 205

His Thr Phe
    210
```

<210> SEQ ID NO 41
<211> LENGTH: 211
<212> TYPE: PRT
<213> ORGANISM: artificial
<220> FEATURE:
<223> OTHER INFORMATION: mutant diaphorase with G149D/G185R/A208V substitutions

<400> SEQUENCE: 41

```
Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Ala Gly Lys Thr Phe Lys Tyr Thr
        115                 120                 125
```

```
Glu Gln Gly Pro Val Gly Leu Leu Thr Asp Lys Lys Ala Leu His Ile
        130                 135                 140

Gln Ala Arg Gly Asp Phe Tyr Ser Glu Gly Pro Ala Ala Glu Met Glu
145                 150                 155                 160

Met Gly His Arg Tyr Leu Ser Val Ile Met Gln Phe Phe Gly Val Pro
                165                 170                 175

Ser Phe Glu Gly Leu Phe Val Glu Arg His Ala Ala Val Pro Glu Lys
                180                 185                 190

Ala Glu Glu Ile Lys Ala Asn Ala Ile Ala Arg Ala Lys Asp Leu Val
        195                 200                 205

His Thr Phe
    210

<210> SEQ ID NO 42
<211> LENGTH: 211
<212> TYPE: PRT
<213> ORGANISM: artificial
<220> FEATURE:
<223> OTHER INFORMATION: mutant diaphorase with F107I/G185R
      substitutions

<400> SEQUENCE: 42

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
                20                  25                  30

Val His Pro Asp His Glu Val Ile His Leu Asp Leu Tyr Lys Glu Tyr
            35                  40                  45

Ile Pro Glu Ile Asp Val Asp Val Phe Ser Gly Trp Gly Lys Leu Arg
        50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Ile Pro Pro Val Leu Lys
            100                 105                 110

Ala Tyr Ile Asp Ala Val Ala Val Ala Gly Lys Thr Phe Lys Tyr Thr
        115                 120                 125

Glu Gln Gly Pro Val Gly Leu Leu Thr Asp Lys Lys Ala Leu His Ile
        130                 135                 140

Gln Ala Arg Gly Gly Phe Tyr Ser Glu Gly Pro Ala Ala Glu Met Glu
145                 150                 155                 160

Met Gly His Arg Tyr Leu Ser Val Ile Met Gln Phe Phe Gly Val Pro
                165                 170                 175

Ser Phe Glu Gly Leu Phe Val Glu Arg His Ala Ala Val Pro Glu Lys
                180                 185                 190

Ala Glu Glu Ile Lys Ala Asn Ala Ile Ala Arg Ala Lys Asp Leu Ala
        195                 200                 205

His Thr Phe
    210

<210> SEQ ID NO 43
<211> LENGTH: 211
<212> TYPE: PRT
<213> ORGANISM: artificial
<220> FEATURE:
<223> OTHER INFORMATION: mutant diaphorase with F107I/G185R/A208V
``` substitutions

<400> SEQUENCE: 43

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Ile Pro Pro Val Leu Lys
            100                 105                 110

Ala Tyr Ile Asp Ala Val Ala Val Ala Gly Lys Thr Phe Lys Tyr Thr
        115                 120                 125

Glu Gln Gly Pro Val Gly Leu Leu Thr Asp Lys Lys Ala Leu His Ile
    130                 135                 140

Gln Ala Arg Gly Gly Phe Tyr Ser Glu Gly Pro Ala Ala Glu Met Glu
145                 150                 155                 160

Met Gly His Arg Tyr Leu Ser Val Ile Met Gln Phe Phe Gly Val Pro
                165                 170                 175

Ser Phe Glu Gly Leu Phe Val Glu Arg His Ala Ala Val Pro Glu Lys
            180                 185                 190

Ala Glu Glu Ile Lys Ala Asn Ala Ile Ala Arg Ala Lys Asp Leu Val
        195                 200                 205

His Thr Phe
    210

<210> SEQ ID NO 44
<211> LENGTH: 211
<212> TYPE: PRT
<213> ORGANISM: artificial
<220> FEATURE:
<223> OTHER INFORMATION: mutant diaphorase with F107I/G185R/Q171P
      substitutions

<400> SEQUENCE: 44

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Ile Pro Pro Val Leu Lys
            100                 105                 110

Ala Tyr Ile Asp Ala Val Ala Val Ala Gly Lys Thr Phe Lys Tyr Thr
        115                 120                 125

```
            115                 120                 125
Glu Gln Gly Pro Val Gly Leu Leu Thr Asp Lys Lys Ala Leu His Ile
    130                 135                 140

Gln Ala Arg Gly Gly Phe Tyr Ser Glu Gly Pro Ala Ala Glu Met Glu
145                 150                 155                 160

Met Gly His Arg Tyr Leu Ser Val Ile Met Pro Phe Phe Gly Val Pro
                165                 170                 175

Ser Phe Glu Gly Leu Phe Val Glu Arg His Ala Ala Val Pro Glu Lys
                180                 185                 190

Ala Glu Glu Ile Lys Ala Asn Ala Ile Ala Arg Ala Lys Asp Leu Ala
            195                 200                 205

His Thr Phe
    210

<210> SEQ ID NO 45
<211> LENGTH: 211
<212> TYPE: PRT
<213> ORGANISM: artificial
<220> FEATURE:
<223> OTHER INFORMATION: mutant diaphorase with V80D/F107I/G185R
      substitutions

<400> SEQUENCE: 45

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
                20                  25                  30

Val His Pro Asp His Glu Val Ile His Leu Asp Leu Tyr Lys Glu Tyr
            35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Asp
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Ile Pro Pro Val Leu Lys
            100                 105                 110

Ala Tyr Ile Asp Ala Val Ala Val Ala Gly Lys Thr Phe Lys Tyr Thr
    115                 120                 125

Glu Gln Gly Pro Val Gly Leu Leu Thr Asp Lys Lys Ala Leu His Ile
    130                 135                 140

Gln Ala Arg Gly Gly Phe Tyr Ser Glu Gly Pro Ala Ala Glu Met Glu
145                 150                 155                 160

Met Gly His Arg Tyr Leu Ser Val Ile Met Gln Phe Phe Gly Val Pro
                165                 170                 175

Ser Phe Glu Gly Leu Phe Val Glu Arg His Ala Ala Val Pro Glu Lys
                180                 185                 190

Ala Glu Glu Ile Lys Ala Asn Ala Ile Ala Arg Ala Lys Asp Leu Ala
            195                 200                 205

His Thr Phe
    210

<210> SEQ ID NO 46
<211> LENGTH: 211
<212> TYPE: PRT
<213> ORGANISM: artificial
<220> FEATURE:
```

<223> OTHER INFORMATION: mutant diaphorase with F107I/K139N/V168L/G185R substitutions

<400> SEQUENCE: 46

| Met | Thr | Asn | Val | Leu | Tyr | Ile | Thr | Ala | His | Pro | His | Asp | Asp | Thr | Gln |
|---|---|---|---|---|---|---|---|---|---|---|---|---|---|---|---|
| 1 | | | | 5 | | | | | 10 | | | | | 15 | |

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Ile Pro Pro Val Leu Lys
            100                 105                 110

Ala Tyr Ile Asp Ala Val Ala Val Ala Gly Lys Thr Phe Lys Tyr Thr
        115                 120                 125

Glu Gln Gly Pro Val Gly Leu Leu Thr Asp Asn Lys Ala Leu His Ile
130                 135                 140

Gln Ala Arg Gly Gly Phe Tyr Ser Glu Gly Pro Ala Ala Glu Met Glu
145                 150                 155                 160

Met Gly His Arg Tyr Leu Ser Leu Ile Met Gln Phe Phe Gly Val Pro
                165                 170                 175

Ser Phe Glu Gly Leu Phe Val Glu Arg His Ala Ala Val Pro Glu Lys
            180                 185                 190

Ala Glu Glu Ile Lys Ala Asn Ala Ile Ala Arg Ala Lys Asp Leu Ala
        195                 200                 205

His Thr Phe
    210

<210> SEQ ID NO 47
<211> LENGTH: 211
<212> TYPE: PRT
<213> ORGANISM: artificial
<220> FEATURE:
<223> OTHER INFORMATION: mutant diaphorase with F150V substitution

<400> SEQUENCE: 47

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Ala Gly Lys Thr Phe Lys Tyr Thr

```
                115                 120                 125
Glu Gln Gly Pro Val Gly Leu Leu Thr Asp Lys Lys Ala Leu His Ile
            130                 135                 140

Gln Ala Arg Gly Gly Val Tyr Ser Glu Gly Pro Ala Ala Glu Met Glu
145                 150                 155                 160

Met Gly His Arg Tyr Leu Ser Val Ile Met Gln Phe Phe Gly Val Pro
                165                 170                 175

Ser Phe Glu Gly Leu Phe Val Glu Gly His Ala Ala Val Pro Glu Lys
            180                 185                 190

Ala Glu Glu Ile Lys Ala Asn Ala Ile Ala Arg Ala Lys Asp Leu Ala
            195                 200                 205

His Thr Phe
    210

<210> SEQ ID NO 48
<211> LENGTH: 211
<212> TYPE: PRT
<213> ORGANISM: artificial
<220> FEATURE:
<223> OTHER INFORMATION: mutant diaphorase with A193E substitution

<400> SEQUENCE: 48

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
                20                  25                  30

Val His Pro Asp His Glu Val Ile His Leu Asp Leu Tyr Lys Glu Tyr
            35                  40                  45

Ile Pro Glu Ile Asp Val Asp Val Phe Ser Gly Trp Gly Lys Leu Arg
        50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Ala Gly Lys Thr Phe Lys Tyr Thr
            115                 120                 125

Glu Gln Gly Pro Val Gly Leu Leu Thr Asp Lys Lys Ala Leu His Ile
            130                 135                 140

Gln Ala Arg Gly Gly Phe Tyr Ser Glu Gly Pro Ala Ala Glu Met Glu
145                 150                 155                 160

Met Gly His Arg Tyr Leu Ser Val Ile Met Gln Phe Phe Gly Val Pro
                165                 170                 175

Ser Phe Glu Gly Leu Phe Val Glu Gly His Ala Ala Val Pro Glu Lys
            180                 185                 190

Glu Glu Glu Ile Lys Ala Asn Ala Ile Ala Arg Ala Lys Asp Leu Ala
            195                 200                 205

His Thr Phe
    210

<210> SEQ ID NO 49
<211> LENGTH: 211
<212> TYPE: PRT
<213> ORGANISM: artificial
<220> FEATURE:
<223> OTHER INFORMATION: mutant diaphorase with F150V/A193E
``` substitutions

<400> SEQUENCE: 49

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Ala Gly Lys Thr Phe Lys Tyr Thr
        115                 120                 125

Glu Gln Gly Pro Val Gly Leu Leu Thr Asp Lys Lys Ala Leu His Ile
    130                 135                 140

Gln Ala Arg Gly Gly Val Tyr Ser Glu Gly Pro Ala Ala Glu Met Glu
145                 150                 155                 160

Met Gly His Arg Tyr Leu Ser Val Ile Met Gln Phe Phe Gly Val Pro
                165                 170                 175

Ser Phe Glu Gly Leu Phe Val Glu Gly His Ala Ala Val Pro Glu Lys
            180                 185                 190

Glu Glu Glu Ile Lys Ala Asn Ala Ile Ala Arg Ala Lys Asp Leu Ala
        195                 200                 205

His Thr Phe
    210

<210> SEQ ID NO 50
<211> LENGTH: 211
<212> TYPE: PRT
<213> ORGANISM: artificial
<220> FEATURE:
<223> OTHER INFORMATION: mutant diaphorase with Y151H/A193E
      substitutions

<400> SEQUENCE: 50

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Ala Gly Lys Thr Phe Lys Tyr Thr

-continued

```
                115                 120                 125
Glu Gln Gly Pro Val Gly Leu Leu Thr Asp Lys Lys Ala Leu His Ile
    130                 135                 140

Gln Ala Arg Gly Gly Phe His Ser Glu Gly Pro Ala Ala Glu Met Glu
145                 150                 155                 160

Met Gly His Arg Tyr Leu Ser Val Ile Met Gln Phe Gly Val Pro
                165                 170                 175

Ser Phe Glu Gly Leu Phe Val Glu Gly His Ala Ala Val Pro Glu Lys
                180                 185                 190

Glu Glu Glu Ile Lys Ala Asn Ala Ile Ala Arg Ala Lys Asp Leu Ala
                195                 200                 205

His Thr Phe
    210

<210> SEQ ID NO 51
<211> LENGTH: 211
<212> TYPE: PRT
<213> ORGANISM: artificial
<220> FEATURE:
<223> OTHER INFORMATION: mutant diaphorase with G122D/A193E
      substitutions

<400> SEQUENCE: 51

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
                20                  25                  30

Val His Pro Asp His Glu Val Ile His Leu Asp Leu Tyr Lys Glu Tyr
                35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
                100                 105                 110

Ala Tyr Ile Asp Ala Val Ala Val Ala Asp Lys Thr Phe Lys Tyr Thr
                115                 120                 125

Glu Gln Gly Pro Val Gly Leu Leu Thr Asp Lys Lys Ala Leu His Ile
    130                 135                 140

Gln Ala Arg Gly Gly Phe Tyr Ser Glu Gly Pro Ala Ala Glu Met Glu
145                 150                 155                 160

Met Gly His Arg Tyr Leu Ser Val Ile Met Gln Phe Gly Val Pro
                165                 170                 175

Ser Phe Glu Gly Leu Phe Val Glu Gly His Ala Ala Val Pro Glu Lys
                180                 185                 190

Glu Glu Glu Ile Lys Ala Asn Ala Ile Ala Arg Ala Lys Asp Leu Ala
                195                 200                 205

His Thr Phe
    210

<210> SEQ ID NO 52
<211> LENGTH: 211
<212> TYPE: PRT
<213> ORGANISM: artificial
<220> FEATURE:
```

<223> OTHER INFORMATION: mutant diaphorase with G149D/A193E/A208V
      substitutions

<400> SEQUENCE: 52

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Ala Gly Lys Thr Phe Lys Tyr Thr
        115                 120                 125

Glu Gln Gly Pro Val Gly Leu Leu Thr Asp Lys Lys Ala Leu His Ile
    130                 135                 140

Gln Ala Arg Gly Asp Phe Tyr Ser Glu Gly Pro Ala Ala Glu Met Glu
145                 150                 155                 160

Met Gly His Arg Tyr Leu Ser Val Ile Met Gln Phe Phe Gly Val Pro
                165                 170                 175

Ser Phe Glu Gly Leu Phe Val Glu Gly His Ala Ala Val Pro Glu Lys
            180                 185                 190

Glu Glu Glu Ile Lys Ala Asn Ala Ile Ala Arg Ala Lys Asp Leu Val
        195                 200                 205

His Thr Phe
    210

<210> SEQ ID NO 53
<211> LENGTH: 211
<212> TYPE: PRT
<213> ORGANISM: artificial
<220> FEATURE:
<223> OTHER INFORMATION: mutant diaphorase with F150V/A193E/A208V
      substitutions

<400> SEQUENCE: 53

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Ala Gly Lys Thr Phe Lys Tyr Thr
            115                 120                 125

Glu Gln Gly Pro Val Gly Leu Leu Thr Asp Lys Lys Ala Leu His Ile
        130                 135                 140

Gln Ala Arg Gly Gly Val Tyr Ser Glu Gly Pro Ala Ala Glu Met Glu
145                 150                 155                 160

Met Gly His Arg Tyr Leu Ser Val Ile Met Gln Phe Phe Gly Val Pro
                165                 170                 175

Ser Phe Glu Gly Leu Phe Val Glu Gly His Ala Ala Val Pro Glu Lys
            180                 185                 190

Glu Glu Glu Ile Lys Ala Asn Ala Ile Ala Arg Ala Lys Asp Leu Val
        195                 200                 205

His Thr Phe
    210

<210> SEQ ID NO 54
<211> LENGTH: 211
<212> TYPE: PRT
<213> ORGANISM: artificial
<220> FEATURE:
<223> OTHER INFORMATION: mutant diaphorase with F150V/A193E/Q171P
      substitutions

<400> SEQUENCE: 54

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Leu Ser Asp Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Ala Gly Lys Thr Phe Lys Tyr Thr
            115                 120                 125

Glu Gln Gly Pro Val Gly Leu Leu Thr Asp Lys Lys Ala Leu His Ile
        130                 135                 140

Gln Ala Arg Gly Gly Val Tyr Ser Glu Gly Pro Ala Ala Glu Met Glu
145                 150                 155                 160

Met Gly His Arg Tyr Leu Ser Val Ile Met Pro Phe Phe Gly Val Pro
                165                 170                 175

Ser Phe Glu Gly Leu Phe Val Glu Gly His Ala Ala Val Pro Glu Lys
            180                 185                 190

Glu Glu Glu Ile Lys Ala Asn Ala Ile Ala Arg Ala Lys Asp Leu Ala
        195                 200                 205

His Thr Phe
    210

<210> SEQ ID NO 55
<211> LENGTH: 211
<212> TYPE: PRT
<213> ORGANISM: artificial

-continued

```
<220> FEATURE:
<223> OTHER INFORMATION: mutant diaphorase with V80D/F150V/A193E
      substitutions

<400> SEQUENCE: 55

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Asp
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110

Ala Tyr Ile Asp Ala Val Ala Val Ala Gly Lys Thr Phe Lys Tyr Thr
        115                 120                 125

Glu Gln Gly Pro Val Gly Leu Leu Thr Asp Lys Lys Ala Leu His Ile
    130                 135                 140

Gln Ala Arg Gly Gly Val Tyr Ser Glu Gly Pro Ala Ala Glu Met Glu
145                 150                 155                 160

Met Gly His Arg Tyr Leu Ser Val Ile Met Gln Phe Phe Gly Val Pro
                165                 170                 175

Ser Phe Glu Gly Leu Phe Val Gly His Ala Ala Val Pro Glu Lys
            180                 185                 190

Glu Glu Glu Ile Lys Ala Asn Ala Ile Ala Arg Ala Lys Asp Leu Ala
        195                 200                 205

His Thr Phe
    210

<210> SEQ ID NO 56
<211> LENGTH: 211
<212> TYPE: PRT
<213> ORGANISM: artificial
<220> FEATURE:
<223> OTHER INFORMATION: mutant diaphorase with K139N/F150V/V168L/A193E
      substitutions

<400> SEQUENCE: 56

Met Thr Asn Val Leu Tyr Ile Thr Ala His Pro His Asp Asp Thr Gln
1               5                   10                  15

Ser Tyr Ser Met Ala Val Gly Lys Ala Phe Ile Asp Thr Tyr Lys Gln
            20                  25                  30

Val His Pro Asp His Glu Val Ile His Leu Asp Leu Tyr Lys Glu Tyr
        35                  40                  45

Ile Pro Glu Ile Asp Val Asp Val Phe Ser Gly Trp Gly Lys Leu Arg
    50                  55                  60

Ser Gly Lys Ser Phe Glu Glu Leu Ser Asp Glu Glu Lys Ala Lys Val
65                  70                  75                  80

Gly Arg Met Asn Glu Leu Cys Glu Gln Phe Ile Ser Ala Asp Lys Tyr
                85                  90                  95

Val Phe Val Thr Pro Met Trp Asn Phe Ser Phe Pro Pro Val Leu Lys
            100                 105                 110
```

-continued

```
Ala Tyr Ile Asp Ala Val Ala Val Ala Gly Lys Thr Phe Lys Tyr Thr
            115                 120                 125
Glu Gln Gly Pro Val Gly Leu Leu Thr Asp Asn Lys Ala Leu His Ile
        130                 135                 140
Gln Ala Arg Gly Gly Val Tyr Ser Glu Gly Pro Ala Ala Glu Met Glu
145                 150                 155                 160
Met Gly His Arg Tyr Leu Ser Leu Ile Met Gln Phe Phe Gly Val Pro
                165                 170                 175
Ser Phe Glu Gly Leu Phe Val Glu Gly His Ala Ala Val Pro Glu Lys
            180                 185                 190
Glu Glu Glu Ile Lys Ala Asn Ala Ile Ala Arg Ala Lys Asp Leu Ala
        195                 200                 205
His Thr Phe
    210

<210> SEQ ID NO 57
<211> LENGTH: 33
<212> TYPE: DNA
<213> ORGANISM: artificial
<220> FEATURE:
<223> OTHER INFORMATION: synthesized primer sense D1 (1)

<400> SEQUENCE: 57
ggaattccat atgatgacaa acgtattgta cat                               33

<210> SEQ ID NO 58
<211> LENGTH: 28
<212> TYPE: DNA
<213> ORGANISM: artificial
<220> FEATURE:
<223> OTHER INFORMATION: synthesized primer antisense D1 (1)

<400> SEQUENCE: 58
cgggatcctt aaaacgtgtg cgccaagt                                     28

<210> SEQ ID NO 59
<211> LENGTH: 33
<212> TYPE: DNA
<213> ORGANISM: artificial
<220> FEATURE:
<223> OTHER INFORMATION: synthesized primer sense D1 (2)

<400> SEQUENCE: 59
ggaattccat atgatgacaa acgtattgta cat                               33

<210> SEQ ID NO 60
<211> LENGTH: 28
<212> TYPE: DNA
<213> ORGANISM: artificial
<220> FEATURE:
<223> OTHER INFORMATION: synthesized primer antisense D1 (2)

<400> SEQUENCE: 60
cgggatcctt aaaacgtgtg cgccaagt                                     28
```